United States Patent [19]
Whayne et al.

[11] Patent Number: 6,014,590
[45] Date of Patent: *Jan. 11, 2000

[54] SYSTEMS AND METHODS EMPLOYING STRUCTURES HAVING ASYMMETRIC MECHANICAL PROPERTIES TO SUPPORT DIAGNOSTIC OR THERAPEUTIC ELEMENTS IN CONTACT WITH TISSUE IN INTERIOR BODY REGIONS

[75] Inventors: James G. Whayne, Saratoga; Sidney D. Fleischman, Menlo Park; Dorin Panescu, Sunnyvale; Thomas F. Kordis, San Jose; David K. Swanson, Mountain View, all of Calif.

[73] Assignee: EP Technologies, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/742,564

[22] Filed: Oct. 28, 1996

Related U.S. Application Data

[63] Continuation-in-part of application No. 08/557,790, Nov. 13, 1995, Pat. No. 5,904,680, which is a continuation-in-part of application No. 08/206,414, Mar. 4, 1974, abandoned.

[51] Int. Cl.⁷ .................................................. A61B 17/39
[52] U.S. Cl. ............................ 607/122; 606/41; 600/374
[58] Field of Search ................................. 606/41, 42, 45, 606/50; 600/372, 374; 607/100–102, 122

[56] References Cited

U.S. PATENT DOCUMENTS

| | | | |
|---|---|---|---|
| 4,660,571 | 4/1987 | Hess et al. | 607/122 |
| 5,228,442 | 7/1993 | Imran | 600/374 |
| 5,255,679 | 10/1993 | Imran | 600/374 |
| 5,324,284 | 6/1994 | Imran | 606/15 |
| 5,409,000 | 4/1995 | Imran | 607/122 |
| 5,411,025 | 5/1995 | Webster, Jr. | 600/374 |
| 5,549,108 | 8/1996 | Edwards et al. . | |
| 5,575,810 | 11/1996 | Swanson et al. | 607/122 |
| 5,702,438 | 12/1997 | Avitall | 607/122 |
| 5,722,401 | 3/1998 | Pietroski et al. | 600/374 |

FOREIGN PATENT DOCUMENTS

| | | |
|---|---|---|
| WO 94/12098 | 6/1994 | WIPO . |
| WO 94/21168 | 9/1994 | WIPO . |
| WO 96/25094 | 8/1996 | WIPO . |

Primary Examiner—Michael Peffley
Attorney, Agent, or Firm—Lyon & Lyon LLP

[57] ABSTRACT

Structures having asymmetric mechanical properties provide enhanced ability to support therapeutic or diagnostic elements in contact with tissue in an interior body region. The support structure includes a first region, which exhibits a first mechanical property affecting tissue contact, and a second region spaced from the first region about the axis, which exhibits a second mechanical property, different than the first mechanical property, affecting tissue contact. In a preferred embodiment, the first and second mechanical properties correlate with stiffness of the respective first and second regions, with the first region being more flexible (i.e., less stiff) than the second region. The first region, due to its greater flexibility, is more conformal to tissue than the second region. The less flexible (i.e., more stiff) second region imparts greater force against the tissue to urge the more flexible first region toward intimate tissue contact. In a preferred embodiment, the more flexible first region carries at least one therapeutic or diagnostic element.

41 Claims, 18 Drawing Sheets

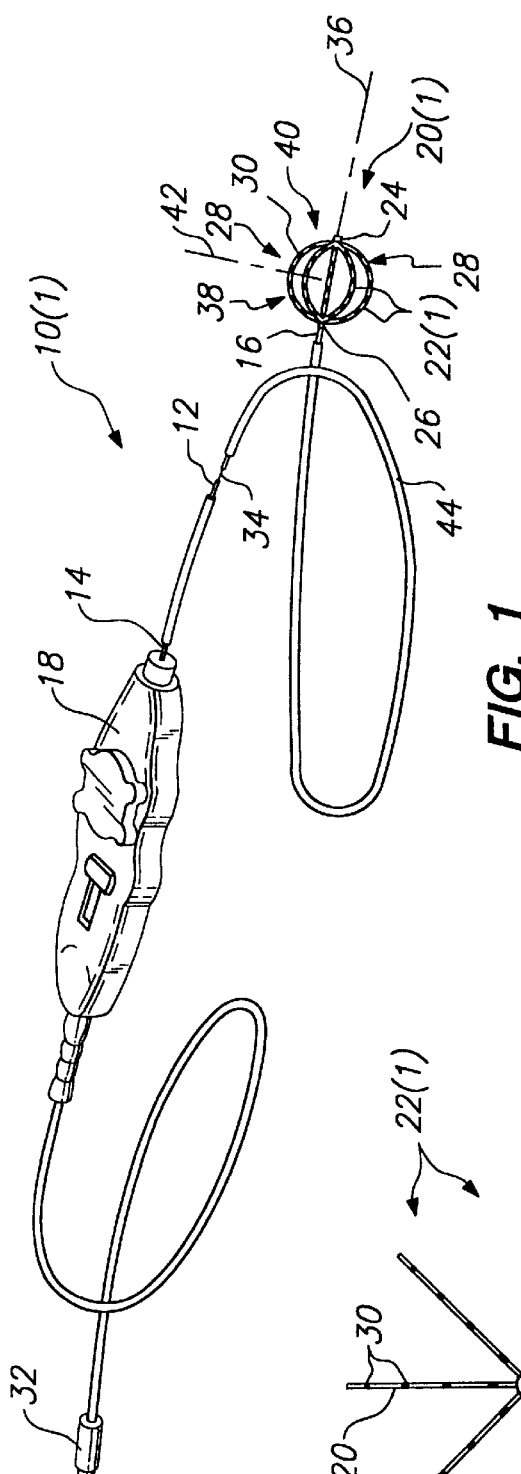
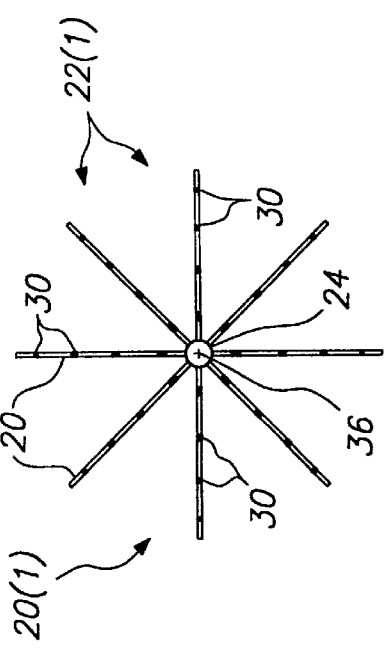
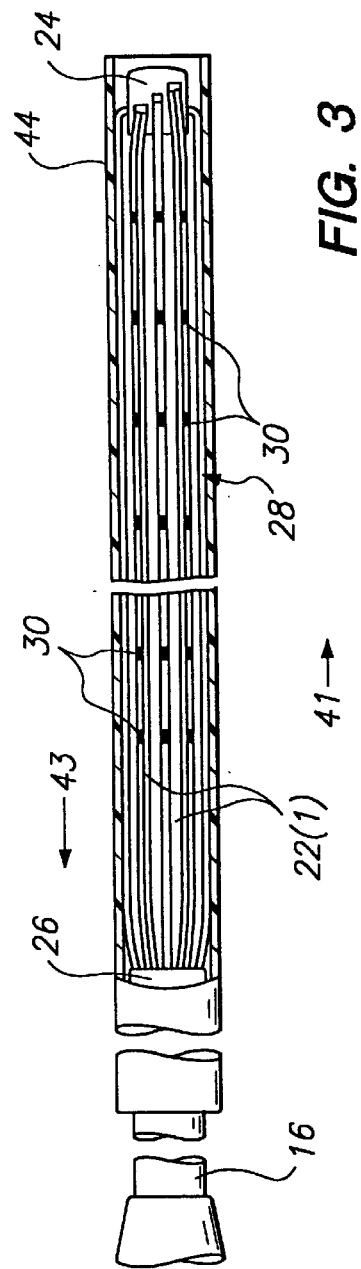
FIG. 1
FIG. 2
FIG. 3

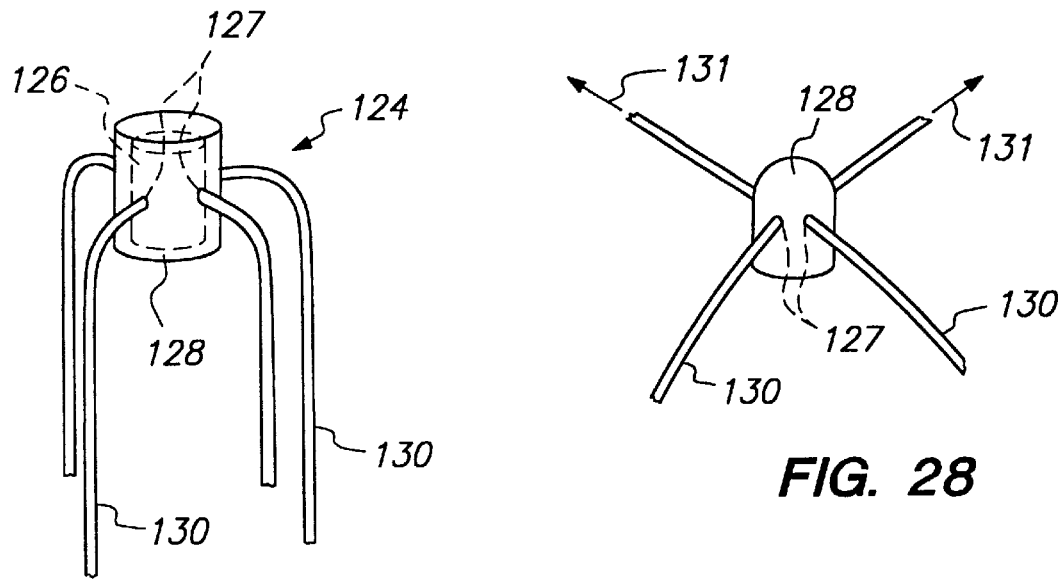
FIG. 27
FIG. 28
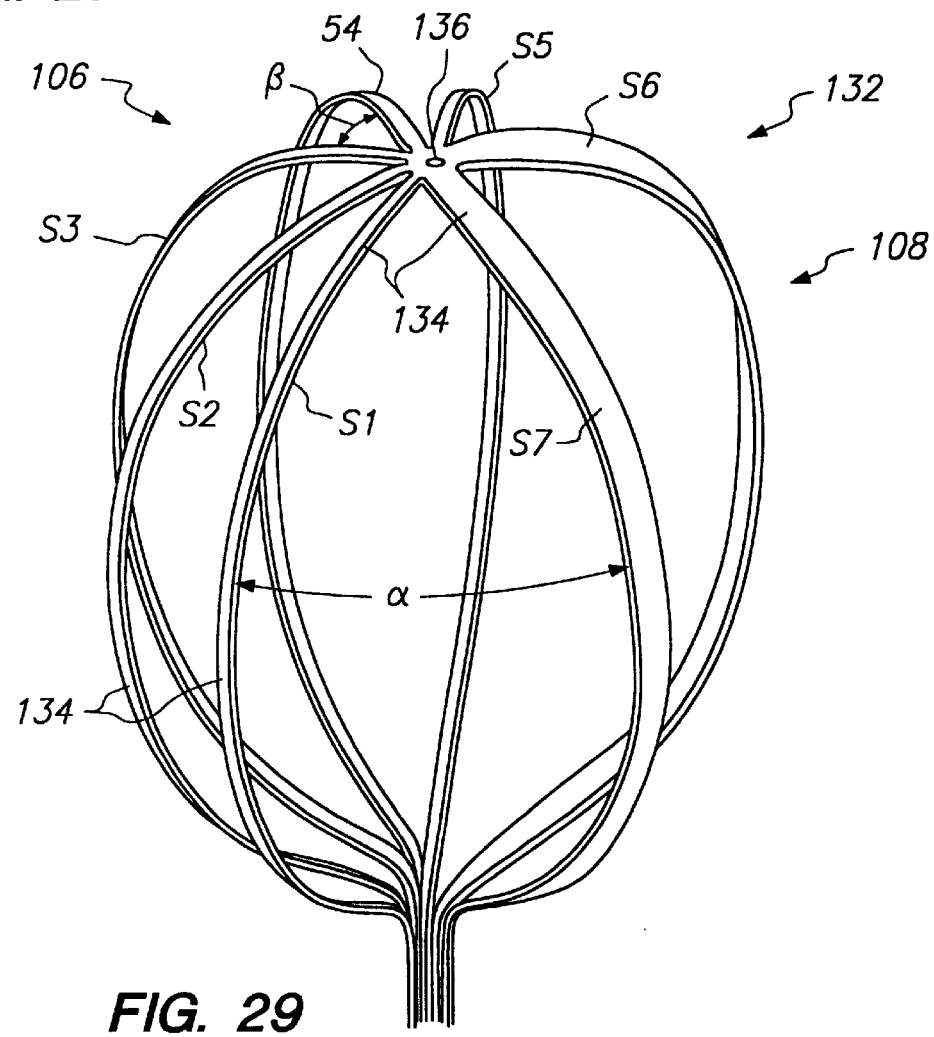
FIG. 29

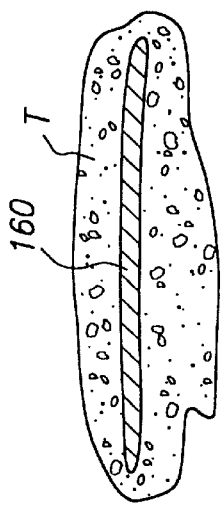
FIG. 32
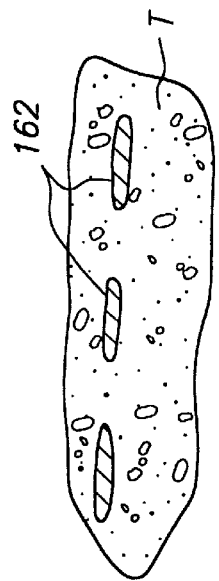
FIG. 33
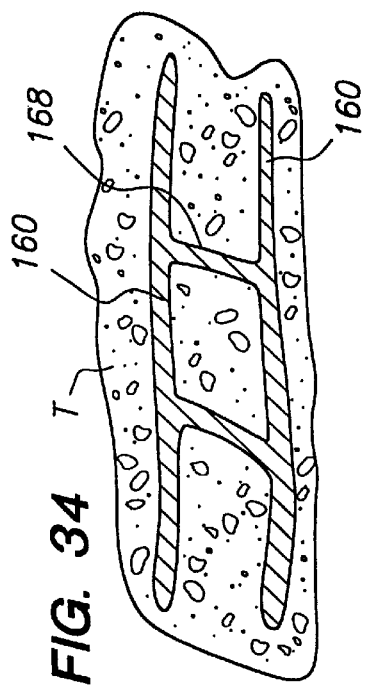
FIG. 34
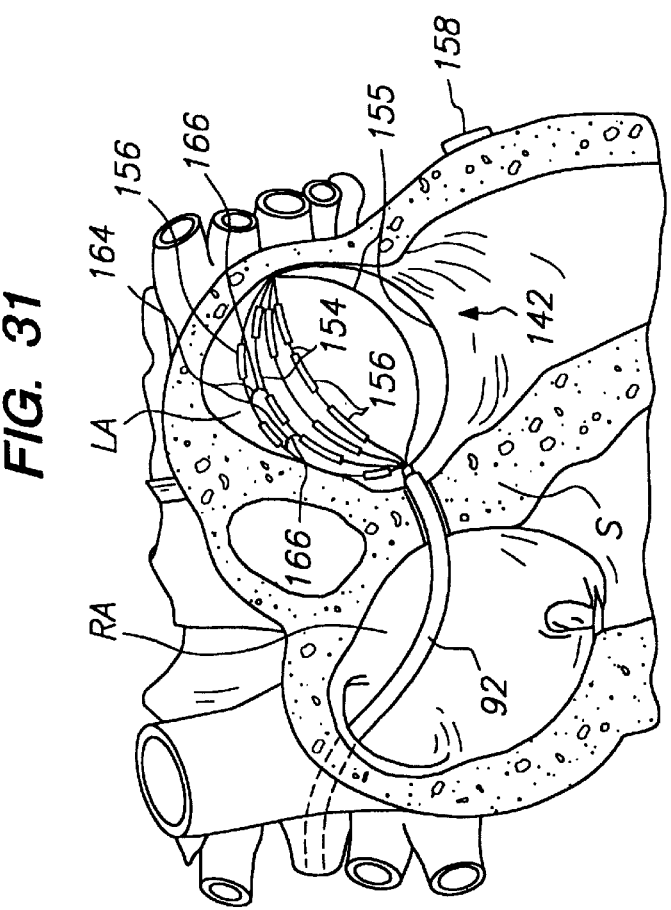
FIG. 31
FIG. 35

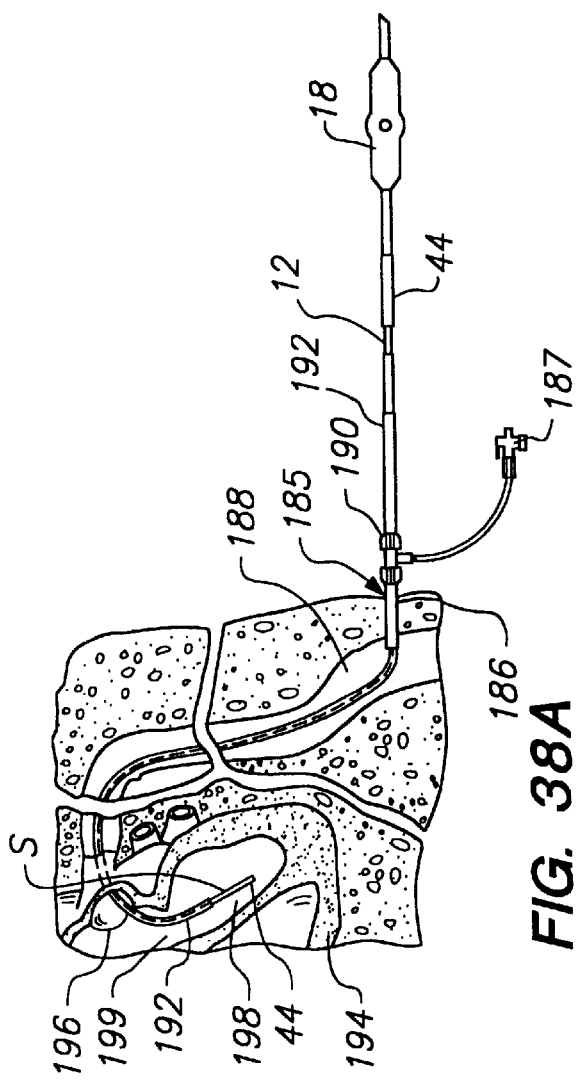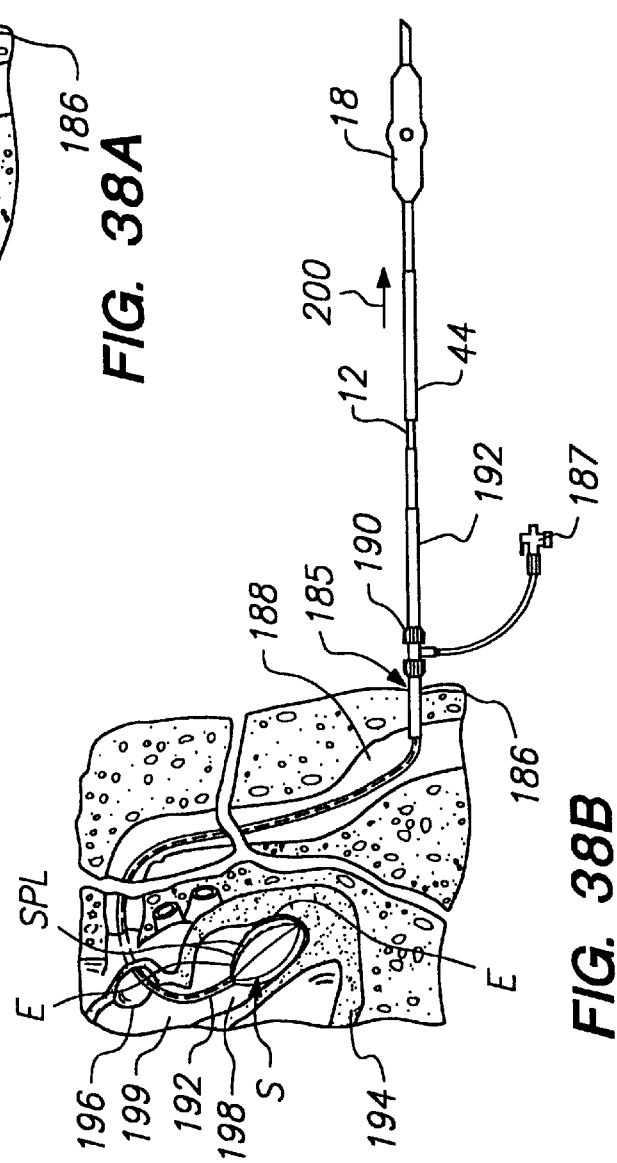

SYSTEMS AND METHODS EMPLOYING STRUCTURES HAVING ASYMMETRIC MECHANICAL PROPERTIES TO SUPPORT DIAGNOSTIC OR THERAPEUTIC ELEMENTS IN CONTACT WITH TISSUE IN INTERIOR BODY REGIONS

RELATED APPLICATION

This application is a continuation-in-part of application Ser. No. 08/557,790, filed Nov. 13, 1995, now U.S. Pat. No. 5,904,680, and entitled "Multiple Electrode Support Structures Having Optimal Bio-Mechanical Characteristics," which is itself a continuation-in-part of application Ser. No. 08/206,414, filed Mar. 4, 1994 (now abandoned) and entitled "Multiple Electrode Support Structures."

FIELD OF THE INVENTION

The invention relates to multiple electrode structures deployed in interior regions of the heart for diagnosis and treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

The need for precise control over the catheter is especially critical during procedures that ablate endocardial tissue within the heart. These procedures, called electrophysiological therapy, are use to treat cardiac rhythm disturbances.

During these procedures, a physician steers a catheter through a main vein or artery into the interior region of the heart that is to be treated. The physician then further manipulates a steering mechanism to place the electrode carried on the distal tip of the catheter into direct contact with the endocardial tissue that is to be ablated. The physician directs energy from the electrode through tissue either to an indifferent electrode (in a uni-polar electrode arrangement) or to an adjacent electrode (in a bi-polar electrode arrangement) to ablate the tissue and form a lesion.

Physicians examine the propagation of electrical impulses in heart tissue to locate aberrant conductive pathways and to identify foci, which are ablated. The techniques used to analyze these pathways and locate foci are commonly called "mapping."

Conventional cardiac tissue mapping techniques introduce several linear electrode arrays into the heart through vein or arterial accesses. There remains a need for improved endocardial mapping, impedance sensing, or ablation techniques using three dimensional, multiple electrode structures.

SUMMARY OF THE INVENTION

The invention provides structures having asymmetric mechanical properties, as well as methods governing the deployment of such structures into interior body regions. The asymmetric mechanical properties enhance the ability of the structures to support therapeutic or diagnostic elements in contact with tissue in the interior body region.

One embodiment provides a support structure having first and second spaced-apart regions. The first region exhibits a first mechanical property affecting tissue contact, and the second region exhibits a second mechanical property, different than the first mechanical property, affecting tissue contact.

In a preferred embodiment, the first and second mechanical properties relate to the stiffness of the first and second regions, with the first region being less stiff (i.e., more flexible) than the second region. In this embodiment, the first region is generally diametrically spaced across the axis of the structure from the second region.

In use, the first region, due to its greater flexibility, is more conformal to tissue than the second region. The less flexible (i.e., more stiff) second region imparts greater force against the tissue to urge the more flexible first region toward intimate tissue contact.

In a preferred embodiment, the more flexible first region carries at least one therapeutic or diagnostic element. In one embodiment, the more stiff second region is free of a therapeutic or diagnostic element.

A preferred embodiment provides an assemblage of spline elements forming a structure for contacting tissue. A number of the spline elements form a first group, in which the spline elements individually possess a first mechanical property. A number of the spline elements form a second group, in which the spline elements individually possess a second mechanical property different than the first mechanical property. In the preferred embodiment, the mechanical properties correlate with stiffness, with the first group of spline elements exhibiting more flexibility (i.e., less stiffness) than the second group of spline elements. In a preferred embodiment, the first group of spline elements number more than the second group of spline elements and are mutually spaced closer together than the second group of spline elements. This arrangement provides a greater density of tissue contact in the first group than the second group. The higher density of spline elements in the first group, due to their greater flexibility, are more conformal to tissue than the second group. The less flexible second group imparts greater force against the tissue to urge the more flexible first group toward intimate tissue contact. In a preferred embodiment, the more flexible first group carries at least one therapeutic or diagnostic element.

Other features and advantages of the inventions are set forth in the following Description and Drawings, as well as in the appended Claims.

BRIEF DESCRIPTION OF THE DRAWINGS

FIG. 1 is a side view of a multiple electrode probe having an electrode support assembly that is both axially and radially symmetric when in its deployed condition;

FIG. 2 is an end view of the electrode support assembly shown in FIG. 1, showing its radial symmetry;

FIG. 3 is an enlarged view, with parts broken away and in cross section, of the distal end of the probe shown in FIG. 1, showing the associated electrode support assembly in a collapsed condition within a sliding outer sleeve;

FIG. 27 is a perspective side view of a distal hub assembly for joining together the distal regions of two flexible spline elements, which are threaded through a length of flexible tubing encapsulated within a resilient sealing material;

FIG. 28 is a perspective side view of the assembly of the distal hub assembly shown in FIG. 28;

FIG. 29 is a perspective side view of an integral, radially asymmetric, axially symmetric support assembly, which possesses asymmetric mechanical properties and which has been cut from a single sheet of material;

FIG. 31 is a perspective view of the interior portion of a heart, which appears in somewhat diagrammatic form for the purpose of illustration, showing a transeptal deployment of a radially asymmetric and axially symmetric multiple electrode support assembly in the left atrium for the purpose of creating long lesion patterns;

FIG. 32 is a diagrammatic representation of a long lesion pattern in tissue, which the electrodes carried by the support assembly shown in FIG. 31 create by additive heating effects;

FIG. 33 is a diagrammatic representation of a segmented lesion pattern in tissue, which multiple electrodes create in the absence of additive heating effects;

FIG. 34 is a diagrammatic representation of a complex long lesion pattern in tissue, which the electrodes carried by the support assembly shown in FIG. 31 create by additive heating effects;

FIG. 35 is a diagrammatic representation of a large lesion pattern in tissue;

FIGS. 38A and 38B are side sectional views, somewhat diagrammatic for the purpose of illustration, showing the deployment of an asymmetric multiple electrode structure within a body region, which is shown as a heart chamber;

Figure 4:
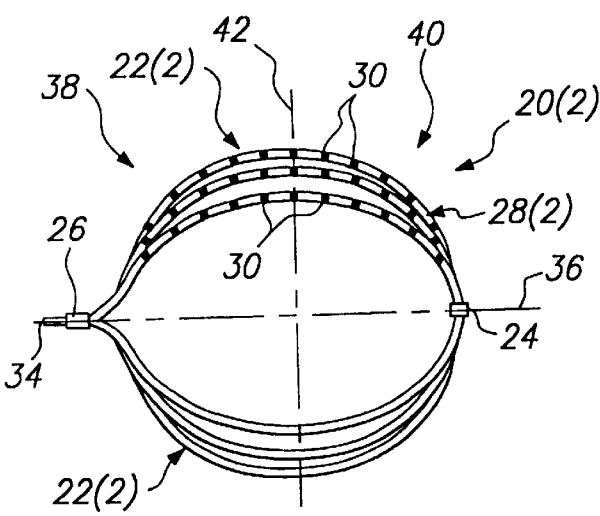
FIG. 4 is a side view of a multiple electrode probe having an electrode support assembly that is axially symmetric but radially asymmetric when in its deployed condition.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Radially and Axially Symmetric Multiple Electrode Probe

FIG. 1 shows a multiple electrode probe 10(1). The probe 10(1) includes a flexible catheter tube 12 with a proximal end 14 and a distal end 16. The proximal end 14 carries an attached handle 18. The distal end 16 carries an electrode support assembly 20(1), shown in side view in FIG. 1 and in end view in FIG. 2.

As FIGS. 1 and 2 show, the support assembly 20(1) comprises an array of flexible spline elements 22(1). Each spline element 22(1) preferably comprises a flexible body made from resilient, inert wire or plastic. Elastic memory material such as nickel titanium (commercially available as NITINOL™ material) can be used. Resilient injection molded plastic or stainless steel can also be used.

The spline elements 22(1) extend longitudinally between a distal hub 24 and a base 26. The base 26 is carried by the distal end 16 of the catheter tube 12. As FIGS. 1 and 2 show, each spline 22(1) is preformed with a convex bias, creating a normally open three dimensional basket structure expanded about a main center axis 36.

The probe 10(1) also includes an electrode circuit assembly 28, one for each spline 22(1). Each circuit assembly 28 comprises an array of multiple electrodes 30. The electrodes 30 are electrically coupled by signal wires 34, which extend through the catheter tube 12, to external the connector 32, which the handle 18 carries (see FIG. 1). Further details of the construction of the electrode circuit assemblies are shown in pending U.S. application Ser. No. 08/206,414, filed Mar. 4, 1994, which is incorporated herein by reference.

In the probe 10(1), the geometry of flexible spline elements 22(1) is radially symmetric about the main axis 36. That is, when viewed from distal hub 24, as FIG. 2 shows, the spline elements 22 uniformly radiate from the main axis 36 at generally equal arcuate, or radial, intervals.

In FIGS. 1 and 2, there are eight, radially symmetric spline elements 22(1), each circumferentially separated by about 45°. This uniform, equal circumferential spacing of the spline elements 22(1) completely about 360° forms a structure that this Specification calls radially symmetric.

The geometry of flexible spline elements 22(1) of the probe 10(1) is also axially symmetric along the main axis 36. That is, when viewed from the side, as FIG. 1 shows, the proximal region 38 and the distal region 40 of each spline assembly 22(1) occupied by the electrodes 30 have essentially the same curvilinear geometry along the main axis 36. Thus, if bent upon itself at its geometric midpoint 42 along the main axis 36, the proximal and distal regions 38 and 40 of the spline assembly 22(1) would essentially overlie each other. This degree of symmetry between the proximal and distal electrode-bearing regions 38 and 40 of the spline elements 22 forms a structure that this Specification calls axially symmetric.

As FIG. 3 shows, in the illustrated and preferred embodiment, the probe 10(1) includes an outer sheath 44 carried about the catheter tube 12. The sheath 44 has an inner diameter that is greater than the outer diameter of the catheter tube 12. As a result, the sheath 44 slides along the catheter tube 12.

As FIG. 3 shows, forward movement (arrow 41 in FIG. 3) advances the slidable sheath 44 completely over the electrode support assembly 20(1). In this position, the slidable sheath 44 compresses and collapses the support assembly 20(1) into a low profile for introduction through a vein or artery to the intended treatment site within the body.

As FIG. 1 shows, rearward movement (arrow 43 in FIG. 3) retracts the slidable sheath 44 away from the support assembly 20(1). This removes the compression force. The freed support assembly 20(1) opens and assumes its three dimensional shape.

When deployed for use (as FIG. 1 shows)—which, in a preferred embodiment, is inside a heart chamber—the support assembly 20(1) of the probe 10(1) holds the electrodes 30 in contact against the endocardium. Due to its radial symmetry, the pattern density of electrodes 30 is generally the same wherever electrode-tissue contact occurs. Thus, the number of electrodes per unit area of endocardium contacted by the electrodes 30 is generally equal throughout the chamber. $$

II. Axially Symmetric/Radially Asymmetric Multiple Electrode Probe

Figure 5:
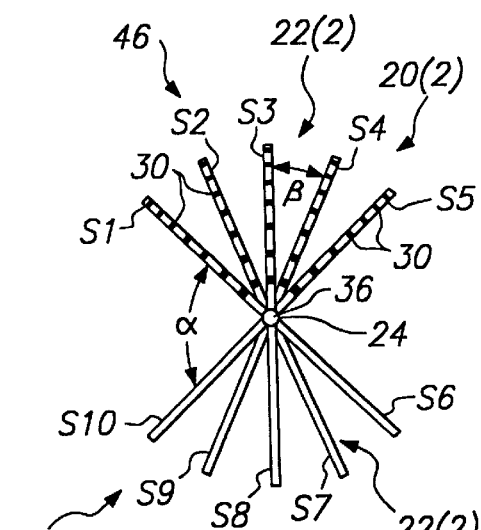
FIG. 5 is an end view of the electrode support assembly shown in FIG. 4, showing its radial asymmetry.

FIGS. 4 and 5 show a multiple electrode support assembly 20(2), which can be attached to the distal end 16 of a catheter tube 12 in the manner support assembly 20(1) shown in FIG. 1. Like the support assembly 20(1), the support assembly 20(2) includes an array of flexible spline elements 22(2) extending longitudinally between a distal hub 24 and a base 26.

For reasons that will be discussed later, due to the radial asymmetry of the assembly 20(2), not all the spline elements 22(2) need to carry electrodes 30. Therefore, as FIGS. 4 and 5 show, electrode circuit assemblies 28(2) are not present on all the spline elements 22(2). Signal wires 34 electrically couple the electrodes 30 that are present to the external connectors 32.

As FIG. 4 shows, the geometry of flexible spline elements 22(2) of the assembly 20(2) is symmetric in an axial sense for the same reasons that the array of spline elements 22(1) shown in FIG. 1 is axially symmetric. FIG. 4 shows the proximal region 38 and the distal region 40 of each spline assembly 22(2) being or capable of being occupied by electrodes 30 to have essentially the same curvilinear geometry along the main axis 36.

However, unlike the assembly 20(1), the geometry of flexible spline elements 22(2) of assembly 20(2) is asymmetric in a radial sense. That is, when viewed from distal hub 24, as FIG. 5 shows, the spline elements 22(2) do not radiate from the main axis 36 at generally equal circumferential intervals. Instead (as FIG. 5 shows), there are at least some adjacent spline elements 22(2) that are circumferentially spaced apart more than other adjacent spline elements 22(2). As described in this Specification, an assembly of spline elements is defined as being "radially asymmetric" when the largest angle measured between two adjacent spline elements in the assembly (designated angle α in FIG. 5) exceeds the smallest angle measured between two other adjacent spline elements (designated angle β in FIG. 5) is greater than 20°.

The particular arrangement shown in FIG. 5 includes ten spline elements 22(2), designated S1 to S10. The asymmetric arrangement shown in FIG. 5 comprises a first discrete group 46 of five adjacent spline elements 22(2) (S1 to S5) and a second discrete group 48 of five adjacent spline elements 22(2) (S6 to S10). The groups 46 and 48 are shown to be diametrically arranged, and each group 46 and 48 occupies an arc of about 90°. Within each group 46 and 48, the adjacent spline elements S1 to S5 and S6 to S10 are circumferentially spaced apart in equal intervals of about 22° (which comprises angle β). However, the spline elements S1/S10 and S5/S6, marking the boundaries between the groups 46 and 48, are circumferentially spaced farther apart, at about 90° (which comprises angle α). This non-uniform circumferential spacing of the spline elements 22(2)—in which angle α minus angle β is about 68° (that is, exceeds 20°)—exemplifies one type of structure that this Specification calls radially asymmetric. In the particular radial asymmetric geometry shown in FIG. 4, the splines S1 to S5 carry electrodes 30, whereas the splines S6 to S10 do not.

Figure 6:
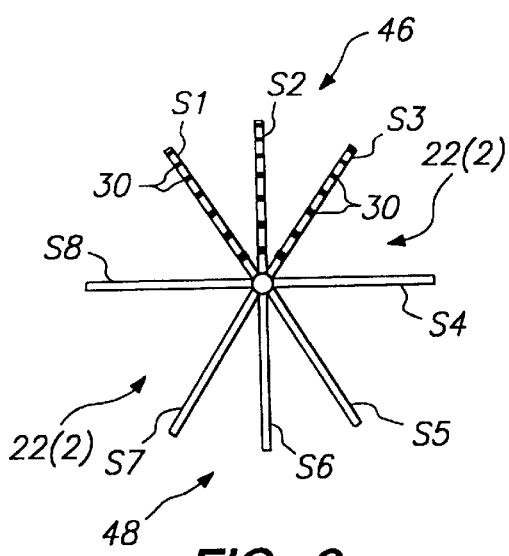
FIG. 6 is an end view of another electrode support assembly that is radially asymmetric.

Other types of structures can also be radially asymmetric. For example, FIG. 6 shows eight spline assemblies S1 to S8 arranged in a radially asymmetric geometry that differs from the one shown in FIG. 5. In FIG. 6, the spline assemblies S1 to S3 (group 46) and S5 to S7 (group 48) are each generally circumferentially spaced apart at equal 30° intervals through an arc of about 60°. However, adjacent spline assemblies S3/S4; S4/S5; S7/S8; and S1/S8 are each circumferentially spaced apart at greater intervals than about 60°. In FIG. 6, the spline assemblies S1 to S3 carry electrodes 30, whereas the remaining spline assemblies S4 to S8 do not.

It should also be appreciated that the groups 46 and 48 of spline assemblies 22(2) need not be diametrically spaced apart (as FIGS. 5 and 6 show), nor do the spline assemblies 22(2) within any given group 46 and 48 need to be equally spaced apart. Radially asymmetric structures are formed whenever the arcuate spacing between any two spline element differs significantly from the arcuate spacing between any two other spline elements. Furthermore, the mounting of electrodes 30 on all or some of the spline assemblies can vary. The particular functional requirements for the assembly 20(2) dictate the particular radial asymmetric geometry selected for the spline elements 22(2), as well as the particular placement of electrode 30 on all or some of the spline elements 22(2).

Figure 51:
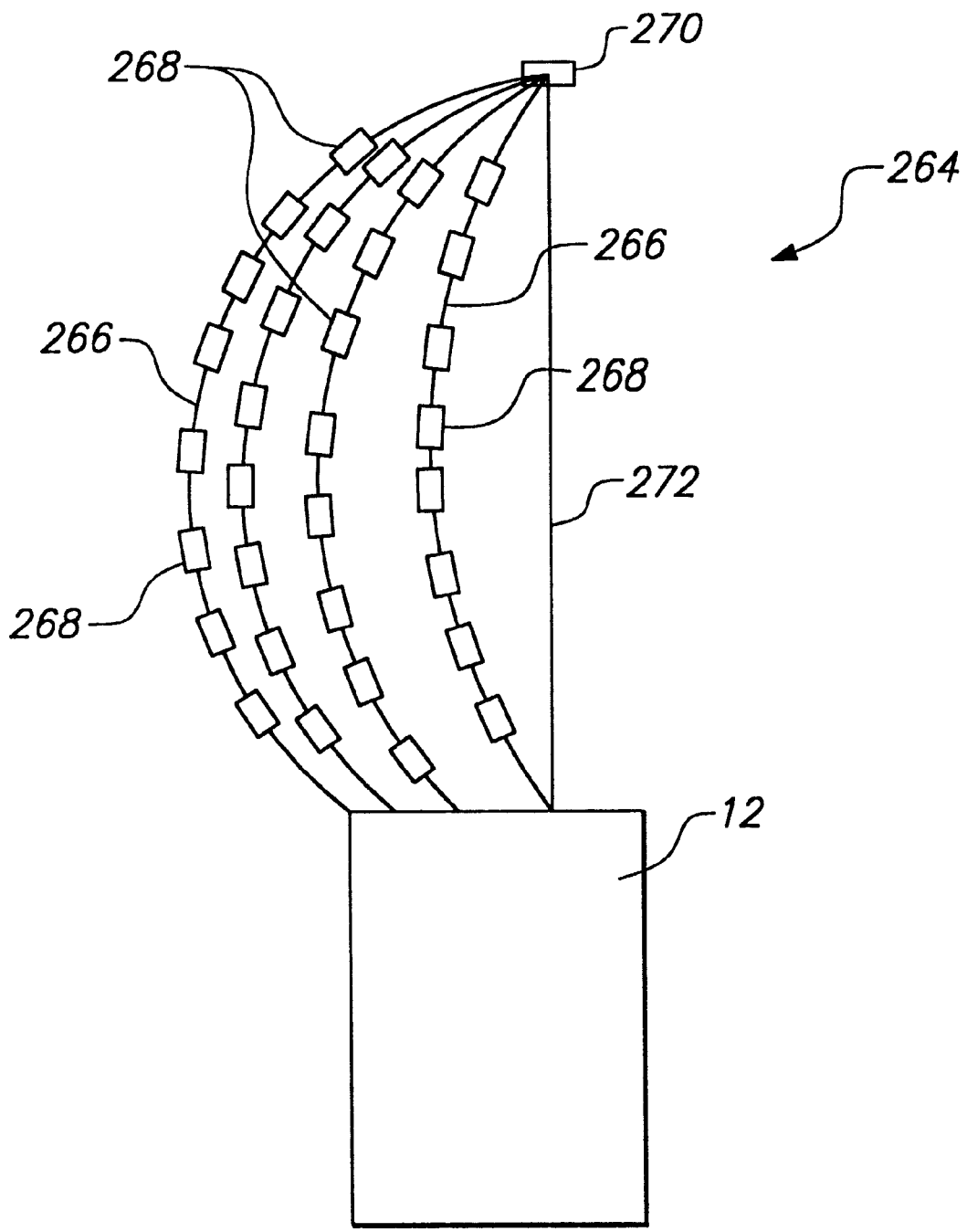
FIG. 51 is a side view, largely diagrammatic, showing a structure for supporting electrodes comprising spline elements arranged in a radially asymmetric geometry in one region of the structure, the other region being free of spline elements.

By way of further example, FIG. 51 shows a spline assembly 264 which is radially asymmetric. The spline assembly 264 includes an array of spline elements 266 arranged in a closely spaced relationship in one region of the assembly 264. The spline elements 266 carry electrodes 268. The remainder of the assembly 264 is free of spline elements and, thus, free of electrodes.

In this arrangement, the spline elements 264 include elastic memory that bias the spline elements 264 toward an outwardly bowed condition. The elastic memory thus presents an outward force against tissue, facilitating intimate contact.

Alternatively, or in combination with elastic memory, the assembly 264 can include a pull wire 272 attached to the distal hub 270, from which all the spline elements 266 radiate. Pulling on the wire 272 bows the spline elements 266 outward, toward tissue, creating an force against tissue contacting the spline elements 266.

A. Structures Having Variable Radial Asymmetry

Figure 42:
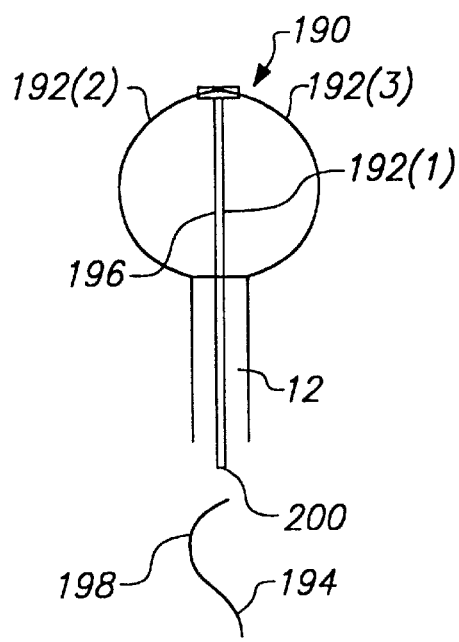
FIGS. 42 to 44 are side views of a structure for supporting electrodes, which includes a slidable memory wire to vary the geometry of the structure from radially symmetric (FIG. 42) to different radially asymmetric geometries (FIGS. 43 and 44)
Figure 43:
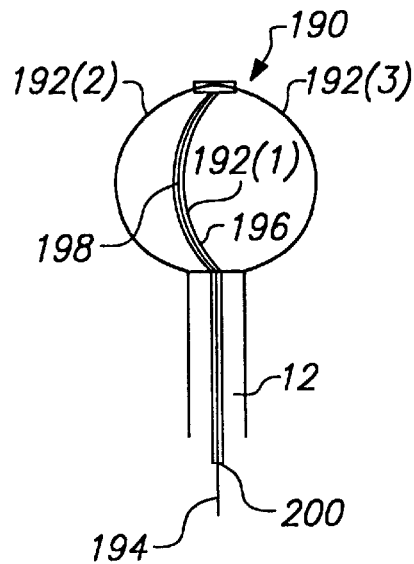
Figure 44:
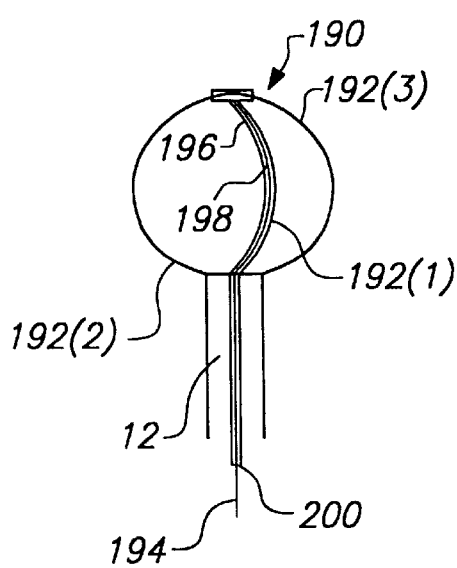

FIGS. 42 to 44 show a support assembly 190, which allows the circumferential spacing of the spline elements (designated 192(1), 192(2), and 192(3)) to be changed by the physician either before or during deployment. The radial geometry of the support assembly 190 is therefore adjustable before and during deployment from a radially symmetric geometry (shown in FIG. 42) to various different asymmetric geometries (shown in FIGS. 43 and 44).

There are various ways to provide variable radial geometries. In the embodiment shown in FIGS. 42 to 44, at least one spline element (designated 192(1)) is enclosed by an exterior sleeve 196 that includes an interior lumen 200. The sleeve 196 extends through the catheter tube 12. The lumen 200 accommodates a sliding wire 194 (see FIG. 42) having elastic memory at its distal end that defines a curve 198.

When confined within the catheter tube 12, the curved distal wire end 198 is urged into a generally straight geometry. When advanced in the lumen 200 beyond the catheter tube 12 and along the spline element 192(1), the elastic memory of the distal wire end 198 bends the spline element 192(1) along the curve 198, as FIG. 43 shows.

The wire 194 can also be rotated within the lumen 200. Rotation of the wire 194 within the lumen 200 shifts the orientation of the curve 198, thereby altering the direction of the bend along the spline element 192(1), as a comparison of FIGS. 43 and 44 show. By adjusting the curve 198 to bend the spline element 192(1) orthogonal to the axis of the structure 190 toward the spline element 192(2) (see FIG. 43), the circumferential spacing between the spline element 192(1) and its neighboring spline element 192(2) is altered. Conversely, by adjusting the curve 198 to bend the spline element 192(1) orthogonal to the axis of the structure 190 toward the spline element 192(3) (see FIG. 44), the circumferential spacing between the spline element 192(1) and its neighboring spline element 192(3) is altered.

A circumferential pattern of spline elements 192(1), 192(2), and 192(3) that was radially symmetric before introduction of the wire 194 (see FIG. 42), thus becomes radially asymmetric after the introduction and rotation of the wire 194 within the spline element 192(1). Rotating the wire 192(1) to shift the orthogonal orientation of the curve 198 (see FIGS. 43 and 44) also shifts the nature of the radial asymmetry of the structure 190.

Figure 45:
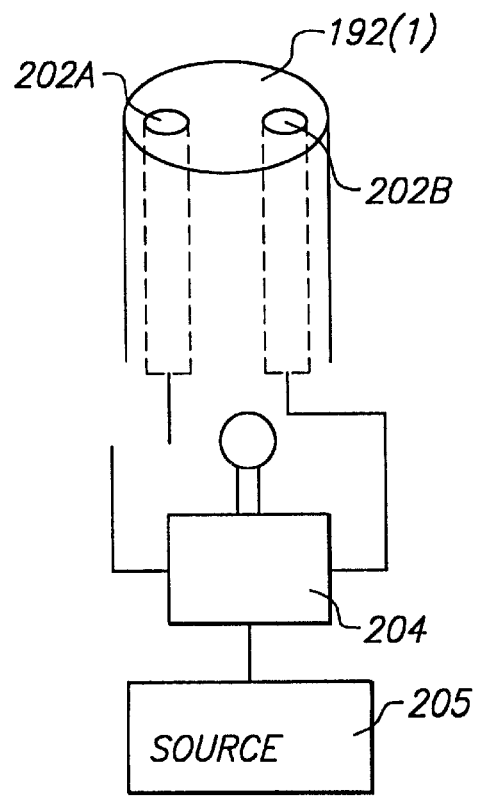
FIG. 45 is a diagrammatic view of a support spline usable in the structure shown in FIG. 42, which includes temperature-activated memory wire to vary the geometry of the structure from radially symmetric (FIG. 42) to different radially asymmetric geometries (FIGS. 43 and 44)

As FIG. 45 shows, formation of the curve 198 can be electrically accomplished in situ by providing two temperature activated memory elements 202A and 202B within one or more of the spline elements 192 (FIG. 45 shows the elements 202A and 202B in spline element 192(1) of the structure shown in FIG. 42).

The elements 202A and B can be formed, for example, from wires or flat strips of nickel titanium alloy. The elements 202A and B are each annealed to a preset, curved shape. The elements 202A and B are cooled and straightened to a shape that conforms to the normal geometry of the spline element.

The elements 202 are coupled to a source 205 of electric current. Current flow through a selected one of the elements 202A or 202B heats the selected element 202A or 202B, causing it to return to its annealed curved shape. Interruption of the current flow allows the element 202A and B to cool and return to its cooled, straightened geometry. A joystick control 204 directs current flow to a selected one of the elements 202A and B.

Further details of the use of electrically controlled temperature-activated memory elements to steer tubular bodies, like catheters, are discussed in McCoy U.S. Pat. No. 4,543,090, which is incorporated herein by reference.

As before described, a circumferential pattern of spline elements 192(1), 192(2), and 192(3) that was radially symmetric before conduction of current by the element 202A becomes radially asymmetric after the element 202A is heated by current flow to bend and reorient the associated spline element 192(1) in one direction orthogonal to the axis of the structure (as FIG. 43 shows). Conduction of current by the element 202B bends and reorients the associated spline element 192(1) in another direction orthogonal to the axis of the structure (as FIG. 44 shows) Use of the joystick control 204 selects which one of the elements 202A or 202B is heated, so that the nature of the radial asymmetry of the structure 190 can be adjusted accordingly.

Figure 46:
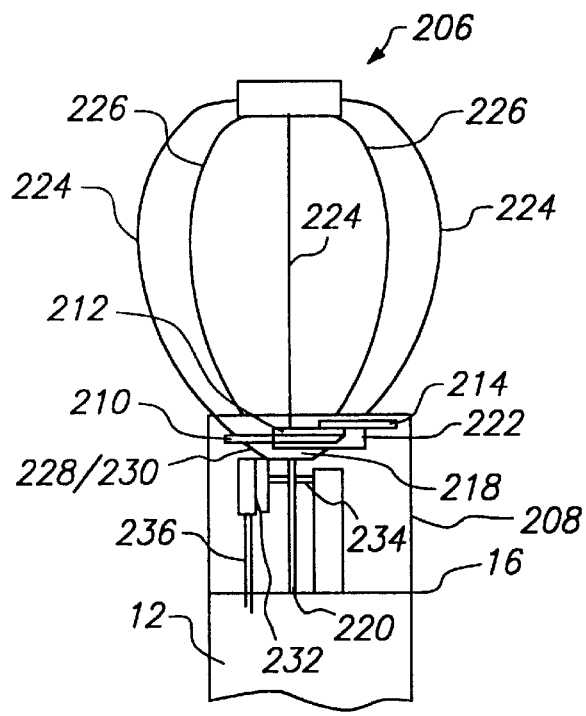
FIG. 46 is a side section view, largely diagrammatic, showing a structure for supporting electrodes, which includes an array of sliding plates to vary the geometry of the structure from radially symmetric to different radially asymmetric geometries.
Figure 47:
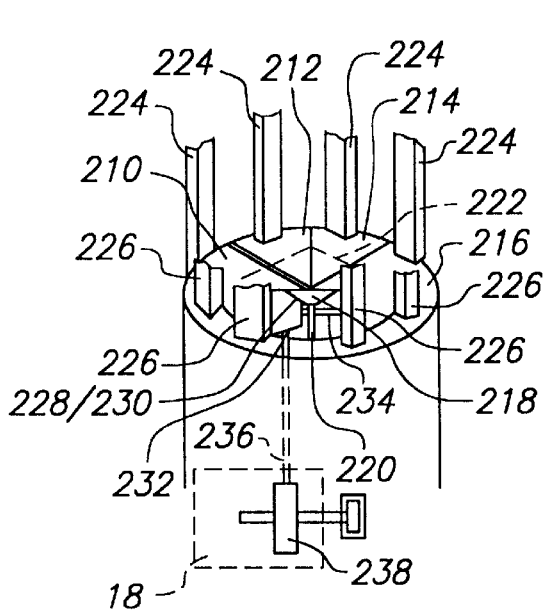
FIG. 47 is a top perspective view of the structure shown in FIG. 46, with the plates spread apart to create a radially symmetric geometry.
Figure 48:
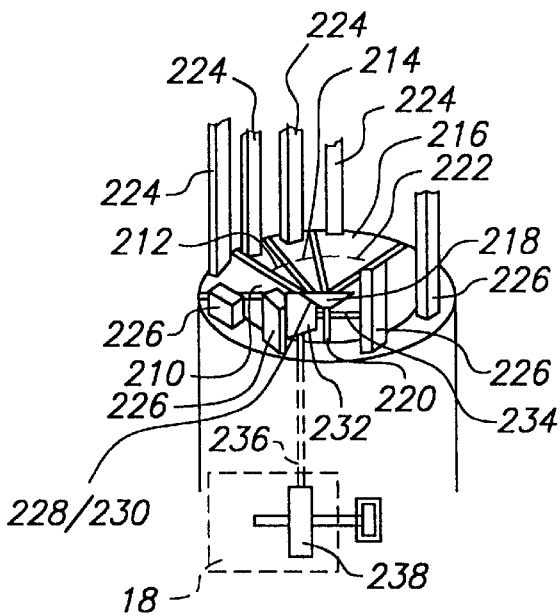
FIG. 48 is a top perspective view of the structure shown in FIG. 46, with the plates stacked together to create a radially asymmetric geometry.

FIGS. 46 to 48 show another alternative way of creating a support assembly 206 having a variable radial asymmetry. In this embodiment, the support assembly 206 includes a base 208 attached to the distal end 16 of the catheter tube 12. The base 208 includes an array of movable plates 210, 212, 214, 216. The plates 210, 212, 212, 214, and 216 are preferably made from stainless steel or other chemically inert metal. The movement of the plates is such that the plate 216 is slidable over the adjacent plate 214; the plate 214 is slidable over the next adjacent plate 212; and the plate 212 is slidable over the next adjacent plate 210. The plate 210 is secured to the base 216 and does not move.

The plates 210, 212, 214, and 216 are coupled to an actuator 218, which rotates about an axle 220. Rotation of the actuator 218 moves the plates 212, 214, and 216 relative to the stationary plate 210.

More particularly, counterclockwise rotation of the actuator 218 causes the movable plates 212, 214, and 216 to slide, one over the other, toward the stationary plate 210. This movement reduces the circumferential spacing between each plate, as FIG. 48 shows, as the plates move together, stacking up one atop the other.

Clockwise rotation of the actuator 218 causes the movable plates 212, 214, and 216 to slide, one over the other, away from the stationary plate 210. This movement enlarges the circumferential spacing between each plate, as FIG. 47 shows, as the plates move apart.

In the preferred embodiment, spring elements 222 couple the stationary plate 210 to each of the movable plates 212, 214, and 216. The spring elements 22 normally urge the plates 212, 214, and 216 toward the stationary plate 210. The spring elements 22 thereby make the movement of the plates 212, 214, and 216 toward and away from the plate 210 more uniform in response to the actuator 218.

The actuator 218 includes a bevel gear surface 228. The gear surface 228 meshes with a bevel gear surface 230 on a second actuator 232, which is carried for rotation about an axle 234. The axle 234 is generally perpendicular to the axle 220.

Wires 236 couple the second actuator 232 to a control element 238, intended to be carried within the proximal handle 18 of the catheter tube 12. Rotation of the control element 238 by the physician clockwise or counterclockwise pulls on the wires 236. Wire tension rotates the second actuator 232 in the same direction as the control element 238 about the axle 234. The gear surfaces 228 and 230 transfer rotation of the second actuator 232 into rotation of the actuator 218 about its axle 220, thereby affecting movement of the plates 210, 212, 214, and 216, as before described, depending upon the direction of rotation.

A spline element 224 is attached to the periphery of each 210, 212, 214, and 216 plate. Other spline elements 226 are secured to the base 208. The spline elements 224 extend from the plates 210, 212, 214, and 216 to a distal hub 226 (as FIG. 46 shows).

As shown in FIG. 47, when the plates 210, 212, 214, and 216 are in their fully expanded condition, the structure 206 possesses a radially symmetric geometry. Movement of the plates 212, 214, and 216 toward the plate 210 in response to counterclockwise rotation of the actuator 218 decreases circumferential spacing between the splines 224, without altering the circumferential spacing between the spline 226. As shown in FIG. 48, when the plates 210, 212, 214, and 216 are moved from their fully expanded condition toward their fully retracted condition, the structure 206 possesses a radially asymmetric geometry.

As before described, the structure 206 exemplifies a radially symmetric pattern of spline elements 224 and 226, which can be caused to become radially asymmetric in a variable way by the physician's operation of the actuator 218.

Figure 49:
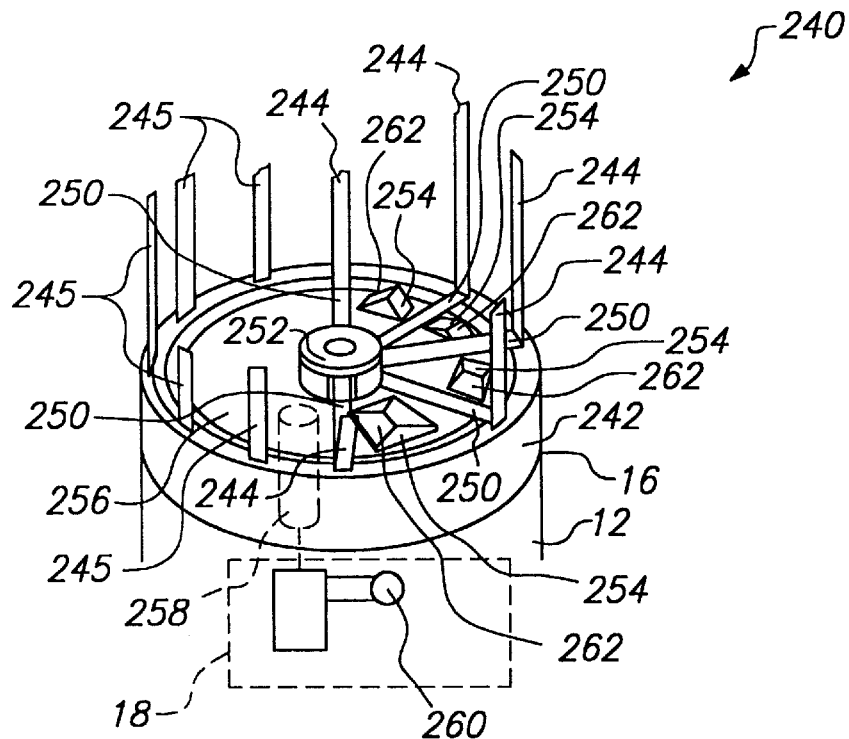
FIG. 49 is a top perspective view showing a structure for supporting electrodes, which includes an elastic joint and a movable array of wedges to vary the geometry of the structure from radially symmetric to different radially asymmetric geometries, the structure being shown with the movable wedges fully advanced near the elastic joint to create a radially symmetric geometry.
Figure 50:
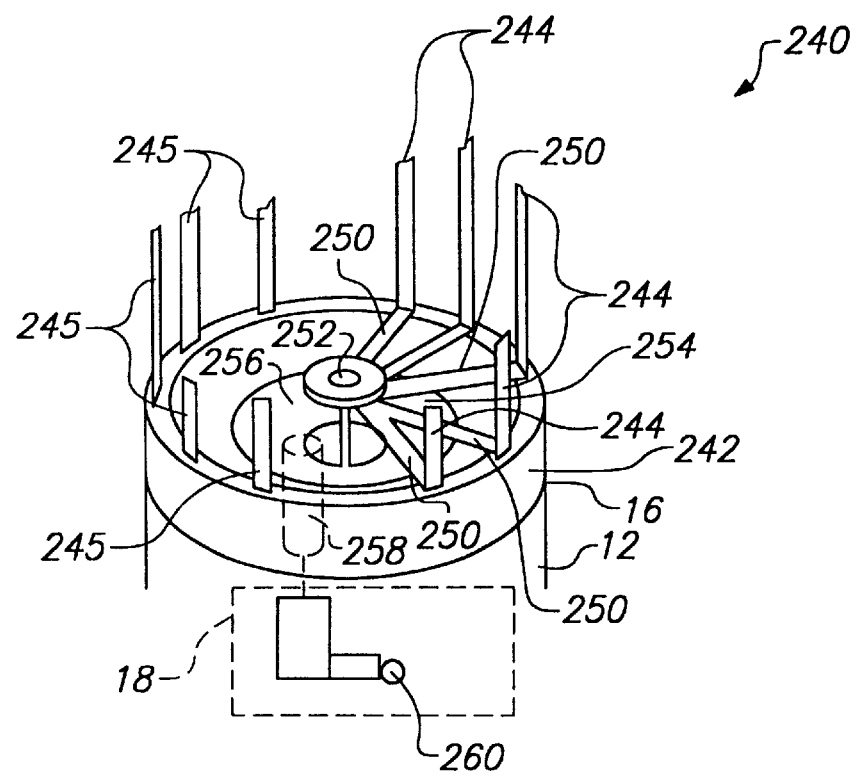
FIG. 50 is a top perspective view of the structure shown in FIG. 49, with the movable wedges fully retracted from the elastic joint to create a radially asymmetric geometry.

FIGS. 49 and 50 show another alternative embodiment of a support assembly 240 possessing variable radial asymmetry. The support assembly 240 includes a base 242 attached to the distal end 16 of the catheter tube 12. The base 242 includes first and second arrays of splines 244 and 245, which radiate from the base to a distal hub (not shown), in the manner shown in FIG. 46.

The proximal ends of the splines 245 are secured in a stationary fashion to the base 242. However, the proximal ends of each spline 244 are mounted for elastic movement orthogonal to the spline axis. In the illustrated embodiment, the proximal ends of the splines 244 are joined to arms 250, which radiate from an elastic center joint 252 supported within the base 242. The elastic joint 252 can be made from nickel titanium, stainless steel, or an elastic polymer. The elastic joint 252 biases the splines 244 toward a first, circumferentially spaced relationship, as FIG. 50 shows.

The first, circumferentially spaced relationship of the movable splines 244 is closer together than the fixed circumferentially spaced relationship of the other splines 245. The support assembly 240 thereby presents a radially asymmetric geometry.

An array of wedges 254 are mounted on an axially movable actuator 256 within the base 242. Each wedge 254 includes oppositely spaced, tapered wedge surfaces 262. The surfaces 262 are preferably coated with a lubricious coating, such as TEFLON™ plastic material.

The actuator 256 is attached to a control shaft 258. The shaft 258 extends through the catheter tube 12 and is coupled to a push-pull control lever 260 housed within the proximal handle 18 carried by the catheter tube 12. Pushing the control level 260 advances the actuator 256 within the base 242 toward the array of splines. Pulling the control lever 260 retracts the actuator 256 within the base 242 away from the array of splines.

As FIG. 49 shows, advancement of the actuator 256 toward the spline array moves the wedges 254 as a unit progressively into the spaces between adjacent splines 244. The tapered wedge surfaces 262 push against adjacent splines 244, overcoming the elasticity of the joint 252. The wedge surfaces 262 progressively push the splines 244 apart. As shown in FIG. 49, the progressively advanced actuator 256 thereby establishes a range of circumferential spacing between the splines 244, which is greater than the normal first circumferential spacing. Advancement of the actuator 256 is stopped when a desired circumferentially spaced relationship within the range is established.

Advancement of the actuator 256 does not affect the circumferential spacing between the other splines 245. When the actuator 256 is fully advanced (see FIG. 49), the splines 244 are circumferentially spaced apart at generally the same distance than the splines 245. A radially symmetric geometry is thereby established.

Retraction of the actuator 256 away from the spline array moves the wedges 254 as a unit progressively out of the space between adjacent splines. The elasticity of the joint 252 urges adjacent splines 244 further together in a range of decreasing circumferential spacing, until the first circumferential spacing established by the joint 252 is reached, as FIG. 50 shows.

As in the other previously described embodiments, the assembly 240 demonstrates how a radially symmetric pattern of spline elements 244 and 245 can be caused to become variably radially asymmetric by operation of an actuator 256.

B. Use of Radially Asymmetric Structures

When deployed, for example, inside a heart chamber, the radially asymmetric support assembly 20(2) holds the electrodes 30 in contact against the endocardium with a varying electrode pattern density. That is, the number of electrodes 30 per unit area of endocardium contacted by electrodes 30 is denser where the group 46 contacts tissue than in other regions of the heart chamber (where there are no electrodes 30 contacting tissue).

In the preferred arrangement shown in FIGS. 4 and 5, the assembly 20(2) provides high density, unidirectional sensing by associating multiple electrodes 30 with only one discrete group 46 of spline assemblies 22(2). In this arrangement, the remaining spline assemblies 22(2), being free of electrodes 30, serve to support and stabilize the electrodes 30 of the group 46 contacting tissue.

Radially asymmetric structures make possible high density mapping, or derivation of an electrical characteristic in localized regions, or pacing in localized regions, without unduly increasing the total number of splines elements 22 or electrode signal wires 34. Systems and methods for deriving an electrical characteristic of tissue, such as tissue impedance, are disclosed, for example, in Panescu et al U.S. Pat. No. 5,494,042, which is incorporated herein by reference. An electrical characteristic is derived by transmitting electrical energy from one or more electrodes into tissue and sensing the resulting flow of electrical energy through the tissue.

III. Radially Symmetric/Axially Asymmetric Multiple Electrode Probe

Figure 7:
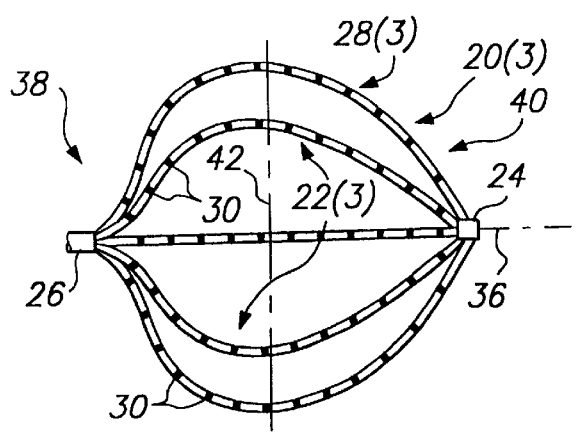
FIG. 7 a side view of a multiple electrode probe having an electrode support assembly that is radially symmetric but axially asymmetric when in its deployed condition.
Figure 8:
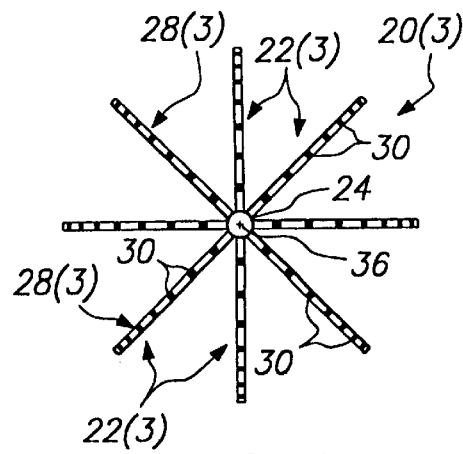
FIG. 8 is an end view of the electrode support assembly shown in FIG. 7, showing its radial symmetry.

FIGS. 7 and 8 show a multiple electrode support assembly 20(3), which is radially symmetric, but axially asymmetric. The assembly 20(3) can be attached to the distal end 16 of a catheter tube 12 in the manner support of assembly 20(1), shown in FIG. 1.

The electrode support assembly 20(3) includes an array of flexible spline elements 22(3), which extend longitudinally between the distal hub 24 and the base 26. The spline elements 22(3) carry electrode circuit assemblies 28(3), each with an array of multiple electrodes 30 coupled by signal wires to the external connectors 32, as already described with reference to FIG. 1.

The geometry of flexible spline elements 22(3) shown in FIGS. 7 and 8 is radially symmetric for the same reasons that the array of spline elements 22(1) of the assembly 20(1) are radially symmetric. As FIG. 8 shows, the spline elements 22 uniformly radiate from the main axis 36 at generally equal arcuate, or circumferential, intervals. In FIGS. 7 and 8, there are eight, radially symmetric spline elements 22(3), each circumferentially separated by about 45°.

However, unlike the assemblies 20(1) and 20(2), the geometry of flexible spline elements 22(3) of the assembly 20(3) is asymmetric in an axial sense. When viewed from the side, as FIG. 7 shows, the proximal electrode-bearing region 38 is not generally symmetric to the distal electrode-bearing region 40. In the arrangement shown in FIG. 7, the spline elements 22(3) flare outward in a substantially perpendicular direction from the base 26, providing a bowl-like proximal region 38. In contrast, the spline elements 22(3) extend outward from the distal hub 24 at a significantly smaller acute angle, providing more of a tapered, conical distal region 40 with a smaller average diameter than the proximal region 38. Thus, if bent upon itself at its geometric midpoint 42 along the main axis 36, the proximal and distal regions 38 and 40 of a given spline assembly 22(3) would not overlie each other. This lack of symmetry between the electrode-bearing regions 38 and 40 along the main axis 36 of the spline elements 22(3) forms a structure that this Specification calls axially asymmetric.

Figure 9:
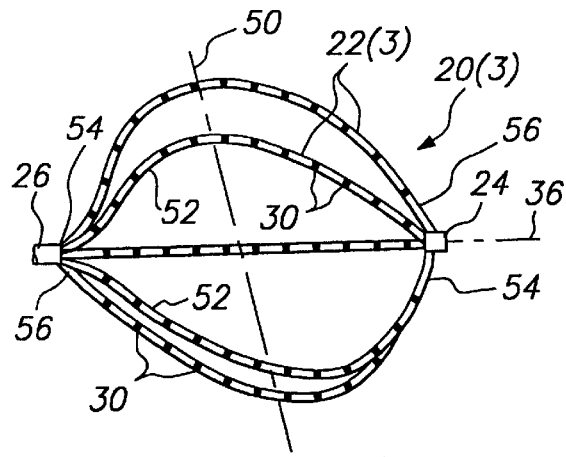
FIG. 9 is a side view of another electrode support assembly that is axially asymmetric.

Many other axially asymmetric structures can be formed. For example, FIG. 9 shows spline elements 22(3), which are J-shaped. Diametrically opposite pairs of the J-shaped spline elements 52 extend from the distal hub 24, with one end 54 of each J-shape element 52 facing the other end 56 of another J-shape element 52. This reverse positioning of J-shape elements 52 forms an electrode support assembly 58 having an elongated, asymmetric bulge along a secondary axis 50, which extends at a non-perpendicular angle across the main axis 36. The reverse positioning of the elements 52 also creates an axial asymmetry that differs among the spline elements. The axial asymmetry of the spline elements 52 shown as occupying the bottom portion of FIG. 9 differs from the axial asymmetry of the spline elements 52 shown as occupying the top portion of FIG. 9.

Axially asymmetric spline elements 22(3) can be preformed from memory elastic materials to assume any desired normally biased, curvilinear shape. Preferably, the axially asymmetric geometry for the assembly 20(3) is selected to best conform to the expected interior contour of the body chamber that the assembly 20(3) will, in use, occupy.

The use of axial asymmetric geometries is particular well suited for deployment for multiple electrode structures within the heart. This is because the interior contour of a heart ventricle differs from the interior contour of a heart atrium. Furthermore, neither atrium nor ventricle is axially symmetric. The ability to provide electrode support assemblies with differing axially asymmetric shapes makes it possible to provide one discrete configuration tailored for atrial use and another discrete configuration tailored for ventricular use.

To assure that the axially asymmetric support assembly 20(3) (or, for that matter, any normally open, preformed support assembly of the type described in this Specification) will uniformly collapse, when desired (for example, by use of the sliding sheath 44), the linear length of each spline element forming the structure must be essentially equal.

When deployed, for example, inside a heart chamber, the axially asymmetric support assembly 20(3) of the probe 10(3) holds the electrodes 30 in intimate contact against the endocardium. Since the support assembly 20(3) is radially symmetric, and each spline assembly 22(3) carries electrodes 30, it establishes a uniform electrode pattern density throughout the chamber. Furthermore, since the axial asymmetry of the support assembly 20(3) is purposely fashioned to generally match the expected interior asymmetric contour of the chamber, the support assembly 20(3) conforms better to the chamber. The axially asymmetric assembly 20(3) provides more stable and more uniformly aligned contact between electrodes 30 and tissue. The axially asymmetric assembly 20(3) is less prone to shift or slide within the chamber in response to the natural contractions, expansions, and twisting forces imposed against it within the dynamic environment of a beating heart.

IV. Both Radially and Axially Asymmetric Multiple Electrode Probe

Figure 10:
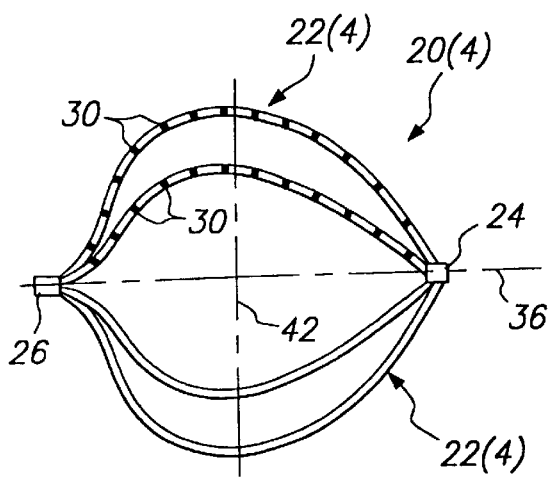
FIG. 10 a side view of a multiple electrode probe having an electrode support assembly that is both axially and radially asymmetric when in its deployed condition.
Figure 11:
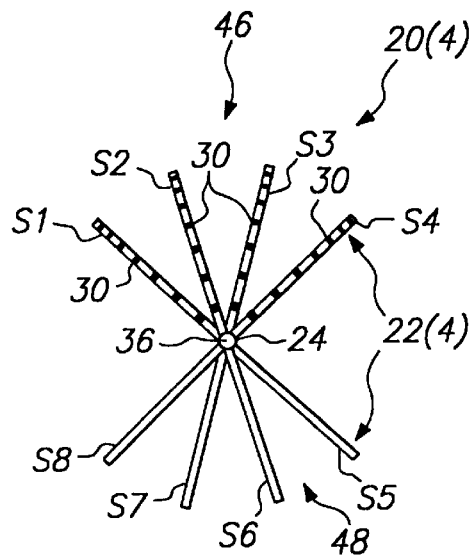
FIG. 11 is an end view of the electrode support assembly shown in FIG. 10, showing its radial asymmetry.

FIGS. 10 and 11 show a multiple electrode support assembly 20(4), which is both radially and axially asymmetric. The electrode support assembly 20(4)can be carried at the distal end 16 of the catheter tube 12, just like the assembly 20(1) shown in FIG. 1.

The assembly 20(4) includes an array of flexible spline elements 22(4) extending longitudinally between the distal hub 24 and the base 26. The spline elements 22(4) provide an array of multiple electrodes 30 coupled by signal wires to the external connectors on the handle 18.

The geometry of the flexible spline elements 22(4) shown in FIGS. 10 and 11 is radially asymmetric for the same reasons that the array of spline elements 22(2) (see FIG. 5) are radially asymmetric. As FIG. 11 shows, eight spline assemblies S1 to S8 are arranged in two discrete groups 46 and 48 of four spline assemblies each. Each group 46 and 48 spans an arc of about 90°, with the splines in each group 46 and 48 equally circumferentially separated by about 30° each (which corresponds to the smallest angle β). The groups 46 and 48 themselves are circumferentially separated by about 90° (which corresponds to the largest angle α). The radial asymmetric criteria is met, since angle α minus angle β is about 60°, i.e., greater than 20°.

As FIG. 11 further shows, only the splines S1 to S4 of the group 46 carry electrodes 30. The splines S5 to S8 of the group 48 are free of electrodes 30 and serve a support function, as previously described. Still, it should be appreciated that electrodes 30 can be mounted on one or more additional splines according to the electrode sensing functions required during use.

The geometry of flexible spline elements 22(4) shown in FIGS. 10 and 11 is also axially asymmetric for the same reasons that the geometries of spline elements shown in FIGS. 8 and 9 are axially asymmetric.

When deployed, for example, inside a heart chamber, the support assembly 20(4) of the probe 10(3) establishes a non-uniform electrode pattern density throughout the chamber. The assembly 20(4) therefore provides a localized high electrode density at the electrodes 30 in the group 46, for mapping, or derivation of an electrical characteristic in localized regions, or pacing in localized regions, while other spline assemblies, free of electrodes (i.e., the group 48), provides support and stabilization. The localized high density achieves better signal resolution and results in less need to interpolate for electrical events that happen to fall between spline assemblies, as the spline assemblies are closer together.

In addition, the axial asymmetry of the support assembly 20(4) better matches the expected interior asymmetric contour of the chamber. The axially asymmetric support assembly 20(4) thereby helps to maintain stable and uniformly aligned contact between the high density electrodes 30 and tissue. Loss of contact between tissue and electrodes, which can produce motion artifacts and a breakdown of intended function, is thereby minimized. Because the contact is more stationary, the physician can be more certain that information obtained from one location during a beat comes from the same location in the next beat.

The ability of the axially asymmetric structure 20(4), and other axially asymmetric structures matched to the expected contour of the targeted site, to maintain intimate contact also minimizes the risk of trauma. Repeated movement and sliding of an electrode support structure across and against the endocardium and interior trabecula and tendonae can lead to perforation or tamponade if the trauma is severe enough. Less severe trauma can still locally injure tissue, increasing the likelihood of clot formation and potential emboli.

V. Criteria for Use

Figure 20:
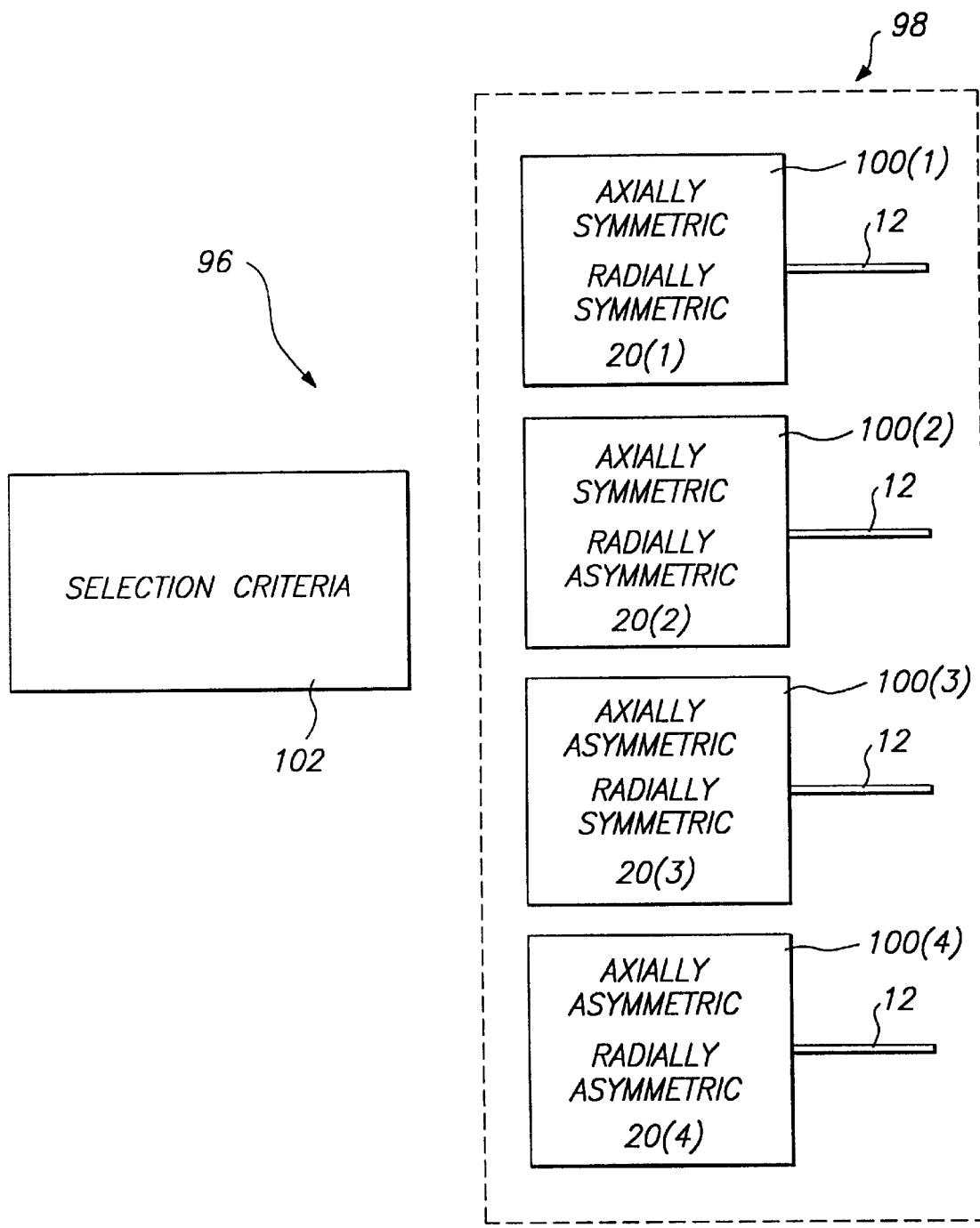
FIG. 20 is a diagrammatic view of a system that comprises a family of electrode support structures of various symmetric and asymmetric geometries, together with criteria suggesting their selection and use by a physician according to functional and physiological factors.

As FIG. 20 shows a system 96 that is based upon the different symmetries of the various support structures 20(1) to 20(4). The system 96 includes a family 98 of multiple electrode structures. In the illustrated embodiment, the family 98 comprises a representative of each of the four geometries of support structures 100(1) to 100(4) described above; namely, (i) an axially and radially symmetric structure 100(1) (exemplified by structure 20(1) shown in FIGS. 1 and 2); (ii) an axially symmetric and radially asymmetric structure 100(2) (exemplified by structure 20(2) shown in FIGS. 4 and 5); (iii) a radially symmetric and axially asymmetric structure 100(3) (exemplified by structure 20(3) shown in FIGS. 7 and 8); and (iv) an axially asymmetric and radially asymmetric structure 100(4) (exemplified by structure 20(4) in FIGS. 10 and 11).

As FIG. 20 shows, each support structure 100(1) to 100(4) is carried at the distal end of a flexible catheter tube 12, in the manner shown in FIG. 1. Each structure 100(1) to 100(4) is individually adapted for selection by a user.

As FIG. 20 further shows, the system 96 also includes an established set of criteria 102. The criteria 102 suggests selection by the user of one support structure 100(1) to 100(4) within the family 98, by correlating use of a given structure 100(1) to 100(4) with an anatomical region, or a disease state, or other diagnostic or therapeutic circumstance.

The criteria 102 can be established in various ways, for example, by the manufacturer(s) of the support structures, the medical community using the support structures, governmental regulatory agencies overseeing licensure of the support structures, or a combination of these. The criteria 102 can be derived from actual and/or predicted functional and physiological requirements, such as the bio-mechanical properties of each support structure; the region of the heart in which the structure will be deployed; the disease state that is to be diagnosed or treated; the type of diagnosis or treatment contemplated; and/or known congenital abnormalities of the patient. The criteria 102 can be based on, for example, empirical data, in vitro or in vivo tests, finite element analysis, anecdotal data, or a combination thereof. The criteria correlates use of one or more geometries of support structures with these functional and/or physiological factors.

The criteria 102 can be presented in various formats. It can be in the form of written suggestions to be read by the physician, or in digital form entered in a computer database or look-up table accessible to the physician, or in audio or video form to be listened to or viewed by the physician.

The following Table exemplifies one embodiment of the criteria 102 presented in written form:

CRITERIA TABLE

SUGGESTED GEOMETRY OF ELECTRODE SUPPORT STRUCTURE

|  | R-Sym | R-Asym | A-Sym | A-Asym | General |
|---|---|---|---|---|---|
| By Anatomic Region |  |  |  |  |  |
| •L Vent Normal | √ |  | √ |  |  |
| •L Vent Ischemic |  | √ | √ |  |  |
| •R Vent |  | √ |  | √ |  |
| •R Vent Outflow Tract | √ |  | √ |  |  |
| •R Atrium |  | √ |  | √ |  |
| •L Atrium |  | √ | √ |  |  |
| By Disease State |  |  |  |  |  |
| •A Fib(I) |  | √ | √-L Atrium | √-R Atrium |  |
| Region Known |  |  |  |  |  |
| •Anomaly is Congenital |  |  |  |  | Based upon Chamber Image |
| When Foci Region Known |  | √ | √-L Vent | √-R Vent |  |

VI. Asymmetric Mechanical Properties

Figure 21:
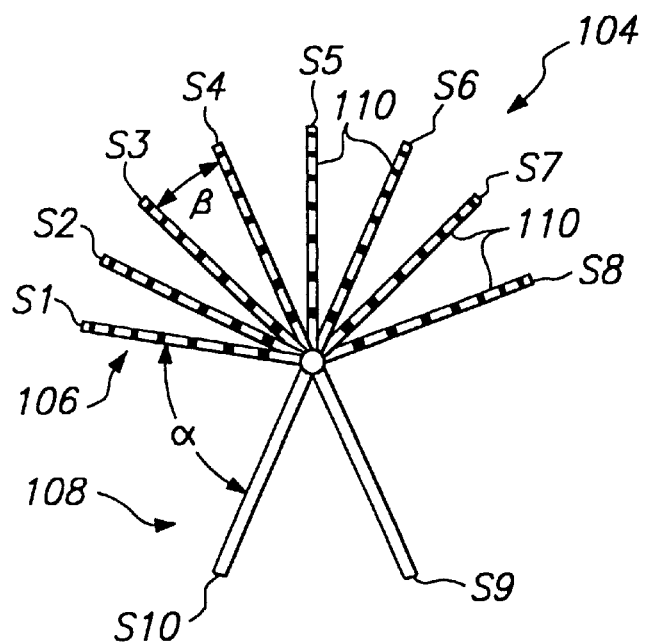
FIG. 21 an end view of a multiple electrode probe having an electrode support assembly that is radially asymmetric when in its deployed condition, and which also possesses asymmetric mechanical properties.
Figure 22:
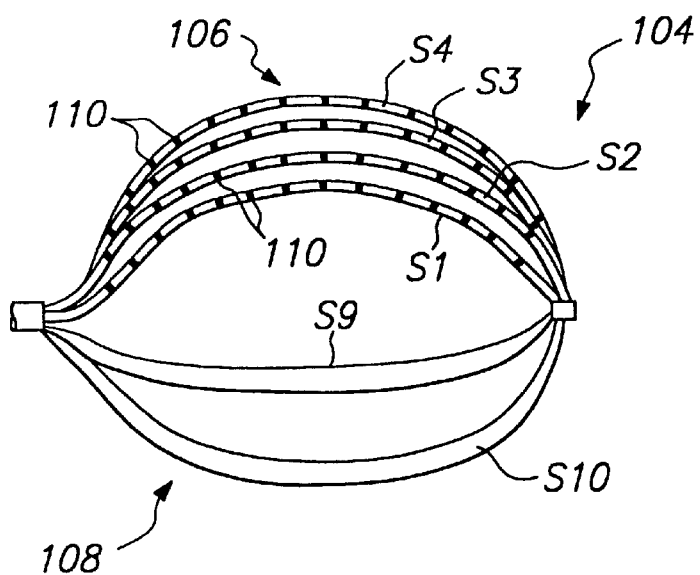
FIG. 22 is a side view of the electrode support assembly shown in FIG. 22.
Figure 23:
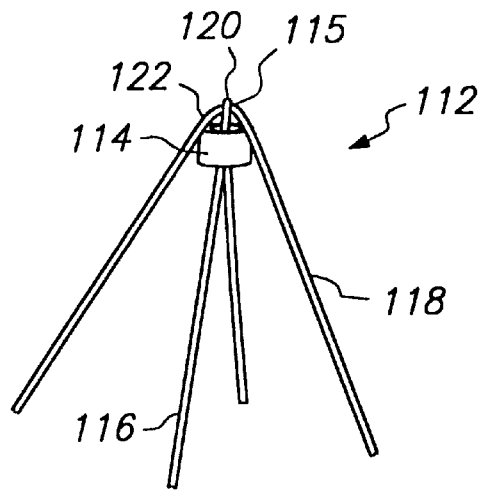
FIG. 23 is a perspective side view of a distal hub assembly for joining together the distal regions of two flexible spline elements, which are held in woven registration by a length of flexible tubing.

FIGS. 21 and 22 show a multiple electrode support structure 104, which is axially symmetric but radially asymmetric for the reasons set forth with respect to the support structure 20(2) shown in FIGS. 4 and 5. The particular arrangement shown in FIGS. 21 and 22 includes ten spline elements, designated S1 to S10. The asymmetric arrangement shown in FIG. 21 comprises a first discrete group 106 of eight adjacent spline elements S1 to S8 and a second discrete group 108 of two adjacent spline elements S9 and S10. Within the first group 106, the adjacent spline elements S1 to S8 are circumferentially spaced apart in equal intervals of about 22° (which comprises angle β). Within the second group 108, the adjacent spline elements S9 and S10 are spaced apart by about 40°. The two groups 106 and 108 are themselves spaced apart by about 70°. Angle α is therefore about 70°, and the angle α minus angle β difference is thereby greater than 20°, which meets the radial asymmetric definition of this Specification.

In the particular radial asymmetric geometry shown in FIGS. 21 and 22, the splines S1 to S8 carry electrodes 110, whereas the splines S9 and S10 do not.

As further shown in FIGS. 21 and 22, the splines S1 to S8 in the first group 106 possess different mechanical properties than the spline S9 and S10 in the second group 108. More particularly, the splines S9 and S10 are each wider in their transverse direction than each of the splines S1 to S8. The splines S9 and S10 are therefore individually more stiff than the individual splines S1 to S8.

The degree of "stiffness" of the splines S1 to S10 can be expressed in terms of a spline radial stiffness function $S_r$. $S_r$ expresses the ratio between radial force ($F_r$) applied to a given spline perpendicular to the axis of the structure 104 and the radial distance ($D_r$) the given spline deflects toward the axis of the structure 104 in response to the radial force. That is:

$$S_r = \frac{F_r}{D_r}$$

The spline radial force function $S_r$ for a given spline can be determined by placing the structure 104 in a cylinder which presses against and restrains all but the given spline 22, which projects through a window in the cylinder. A pin applies force perpendicular to the mid portion of the given spline. A transducer coupled to the pin measures the force $F_r$ exerted against the spline at successive points of radial deflection $D_r$ from the spline's normal rest position in the structure 104. Radial forces $F_r$ can be plotted as a function of radial deflections $D_r$ for the given spline. The slope of the resulting plot is the radial stiffness function $S_r$ for the given spline. The function $S_r$ is expressed in terms of units of force (for example, in grams) per unit of deflection (for example, in inches).

Lower values of $S_r$ indicate lower radial stiffness values and indicate a better ability to deform and create intimate contact along the contour of the endocardium without damage to tissue.

The geometry of the support structure 104 therefore presents the one group 106 of closely spaced spline elements S1 to S8, which are more flexible (i.e., which individually have a lower radial stiffness value $S_r$) than the other group 108 of less closely spaced spline elements S9 and S10 (which individual exhibit a higher radial stiffness value $S_r$ than the spline elements S1 to S8).

The group 106 of more flexible splines S1 to S8 carry the electrodes 110 and, due to their greater flexibility, are more conformal to tissue than the group 108 of splines S9 and S10, which do not carry electrodes. On the other hand, the less flexible group 108 of splines S9 and S10 individually impart greater force against the tissue, thereby urging the other, more flexible splines S1 to S8 and their electrodes 110 toward intimate tissue contact. However, since the tissue contact force ($F_C$) of the spline elements S9 and S10 in the second group 108 is applied over a relatively large surface area ($A_c$), the tissue pressure function $T_P$ is lessened, where $T_P$ is expressed as follows:

$$T_p = \frac{F_c}{A_C}$$

The quantity $T_P$ is a determinant of tissue trauma. Trauma caused by contact force exerted on small, localized area can be mediated by distributing the same contact force over a larger contact area, thereby reducing contact pressure.

The structure 104 shown in FIGS. 21 and 22 therefore provides asymmetric mechanical properties in different regions of the tissue contact. The asymmetric mechanical properties serve to establish and maintain balanced, intimate contact between a high density of electrodes 110 and tissue in a way that minimizes trauma.

VII. Asymmetric Ablation Structures

A. Long Lesions

As the foregoing Criteria Table shows, radially asymmetric electrode structures are well suited for diagnostic or therapeutic use in the atrial regions of the heart. This is because the location of anatomical obstacles that cause abnormal, irregular heart rhythm, called atrial fibrillation, are known with respect to anatomical landmarks within the left or right atrium. Spline density can thereby be concentrated to contact these known obstacles, so that localized ablation can be performed.

In FIG. 31, a transeptal deployment is shown, from the right atrium (RA), through the fossa ovalis at the septum (S), into the left atrium (LA), where a radial asymmetric support structure 142 is located for use. In conformance with the foregoing Criteria Table, the structure 142 occupying the left atrium is axially symmetric.

The more closely radially spaced longitudinal splines 154 of the structure 142 carry an array of multiple electrodes 156. The electrodes 156 serve as transmitters of ablation energy. The less closely radially spaced longitudinal splines 155 do not carry electrodes 156.

The electrodes 156 are preferably operated in a uni-polar mode, in which the radio frequency ablation energy transmitted by the electrodes 156 is returned through an indifferent patch electrode 158 externally attached to the skin of the patient. Alternatively, the electrodes 156 can be operated in a bi-polar mode, in which ablation energy emitted by one or more electrodes 156 is returned an adjacent electrode 158 on the spline 154.

The size and spacing of the electrodes 156 shown in FIG. 31 are purposely set for creating continuous, long lesion patterns in tissue. FIG. 32 shows a representative long, continuous lesion pattern 160 in tissue T, which is suited to treat atrial fibrillation. Continuous, long lesion patterns 160 are formed due to additive heating effects when RF ablation energy is applied in a uni-polar mode simultaneously to the adjacent electrodes 156, provided the size and spacing requirements are observed. The additive heating effects cause the lesion pattern 160 to span adjacent, spaced apart electrodes 156, creating the desired elongated, long geometry, shown in FIG. 32. The additive heating effects will also occur when the electrodes 156 are operated simultaneously in a bipolar mode between electrodes 156, again provided the size and spacing requirements are observed.

The additive heating effects between spaced apart electrodes 156 intensify the desired therapeutic heating of tissue contacted by the electrodes 156. The additive effects heat the tissue at and between the adjacent electrodes 156 to higher temperatures than the electrodes 156 would otherwise heat the tissue, if conditioned to individually transmit energy to the tissue, or if spaced apart enough to prevent additive heating effects.

When the spacing between the electrodes 156 is equal to or less than about 3 times the smallest of the diameters of the electrodes 156, the simultaneous emission of energy by the electrodes 156, either bipolar between the segments or unipolar to the indifferent patch electrode, creates the elongated continuous lesion pattern 160 shown in FIG. 32 due to the additive heating effects. Conversely, when the spacing between the electrodes 156 is greater than about 5 times the smallest of the diameters of the electrodes 156, the simultaneous emission of energy by the electrodes 156, either bipolar between segments or unipolar to the indifferent patch electrode, does not generate additive heating effects. Instead, the simultaneous emission of energy by the electrodes 28 creates an elongated segmented, or interrupted, lesion pattern 162 in the contacted tissue area T, as shown in FIG. 33.

Alternatively, when the spacing between the electrodes 156 along the contacted tissue area is equal to or less than about 2 times the longest of the lengths of the electrodes 156, the simultaneous application of energy by the electrodes 156, either bipolar between electrodes 156 or unipolar to the indifferent patch electrode, also creates an elongated continuous lesion pattern 160 (FIG. 32) due to additive heating effects. Conversely, when the spacing between the electrodes 156 along the contacted tissue area is greater than about 3 times the longest of the lengths of the electrodes 156, the simultaneous application of energy, either bipolar between electrodes 156 or unipolar to the indifferent patch electrode, creates an elongated segmented, or interrupted, lesion pattern 162 in tissue T (FIG. 33).

In the embodiment shown in FIG. 31, the radially asymmetric structure 142 also includes periodic bridge splines 164. The bridge splines 164 are soldered or otherwise fastened to the adjacent longitudinal splines 154. The bridge splines 164 carry electrodes 166, or are otherwise made to transmit ablation energy by exposure of electrically conductive material. Upon transmission of ablation energy, the bridge splines 166 create long transverse lesion patterns 168 in tissue T (shown in FIG. 34) that span across the long longitudinal lesion patterns 160 created by the adjacent splines 154. The transverse lesions 168 link the longitudinal lesions 160 to create complex lesion patterns that emulate the patterns formed by incisions during an open heart, surgical maze procedure.

Further details of the creation of complex long lesion patterns in the treatment of atrial fibrillation are found in copending U.S. application Ser. No. 08/566,291, filed Dec. 1, 1995, and entitled "Systems and Methods for Creating Complex Lesion Patterns in Body Tissue," which is incorporated herein by reference.

The electrode elements 156 can be assembled in various ways. They can, for example, comprise multiple, generally rigid electrode elements arranged in a spaced apart, segmented relationship along the spline elements 154. The segmented electrodes can each comprise a solid ring of conductive material, like platinum, which is pressure fitted about the spline element 154. Alternatively, the electrode segments can comprise a conductive material, like platinum-iridium or gold, coated upon the spline element 154 using conventional coating techniques or an ion beam assisted deposition (IBAD) process. In a preferred embodiment, spaced apart lengths of closely wound, spiral coils are wrapped about the spline element 154 to form an array of generally flexible electrodes 156. The coils are made of electrically conducting material, like copper alloy, platinum, or stainless steel. The electrically conducting material of the coils can be further coated with platinum-iridium or gold to improve its conduction properties and biocompatibility.

In another embodiment, the electrodes 156 comprise elongated, porous bodies holding a medium containing ions that is coupled to a source of radio frequency energy. The porous bodies enable ionic transport of the radio frequency energy to tissue, which electrically heats the tissue to cause the desired lesion. The use of porous electrode bodies to create lesions in body tissue is disclosed in greater detail in copending U.S. patent application Ser. No. 08/631,575, filed Apr. 12, 1996 and entitled "Tissue Heating and Ablation Systems and Methods Using Porous Electrode Structures," which is incorporated herein by reference.

B. Large Lesions

The elimination of ventricular tachycardia (VT) substrates is thought to require significantly larger lesions, with a penetration depth greater than 1.5 cm, a width of more than 2.0 cm, with a lesion volume of at least 1 cm$^3$. There also remains the need to create lesions having relatively large surface areas with shallow depths. FIG. 35 exemplifies the geometry of a typical larger surface area lesion 144 in tissue T.

Figure 36:
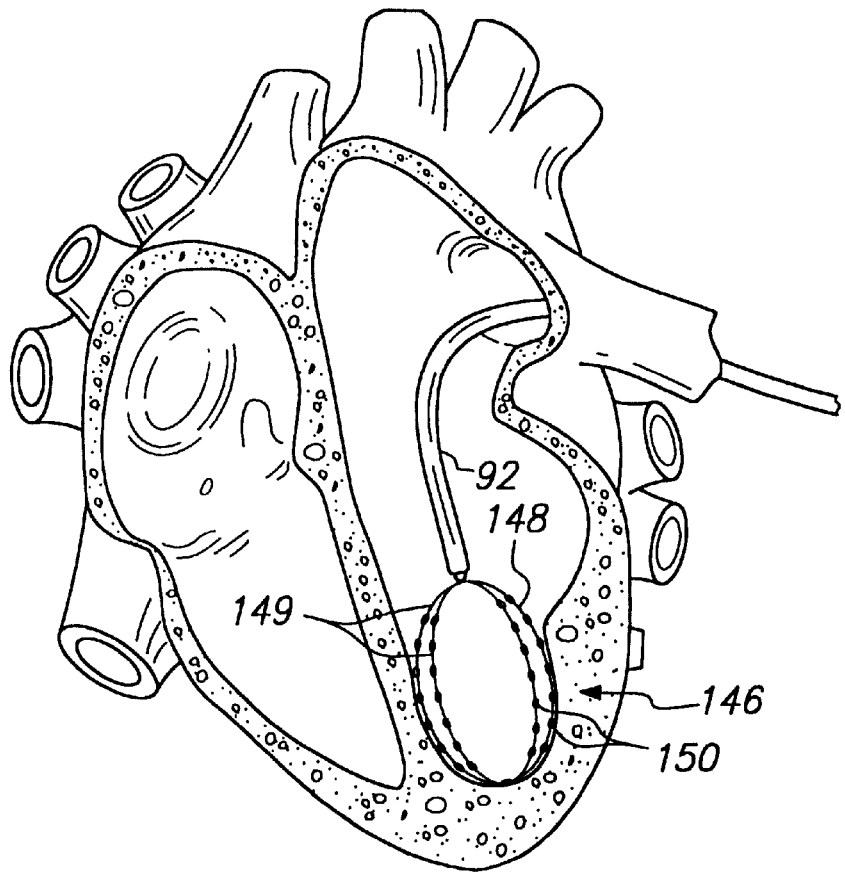
FIG. 36 is a perspective view of the interior portion of a heart, which appears in somewhat diagrammatic form for the purpose of illustration, showing deployment of a radially asymmetric and axially symmetric multiple electrode support assembly in the left ventricle for the purpose of creating a large lesion pattern.
Figure 37:
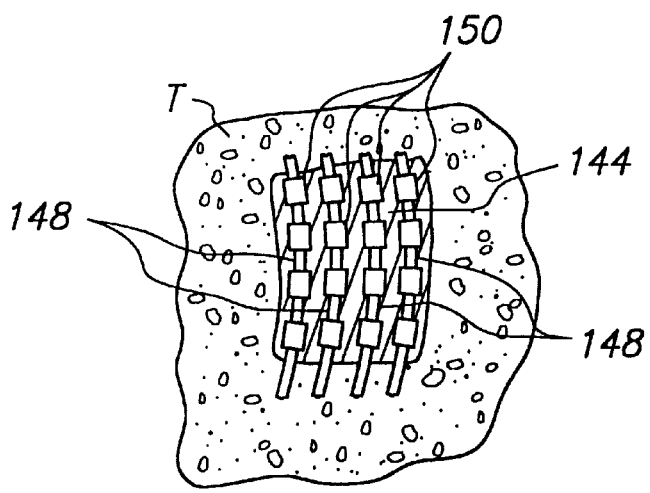
FIG. 37 is a diagrammatic representation of a large lesion pattern in tissue, which the electrodes carried by the support assembly shown in FIG. 36 create by additive heating effects.

Radially asymmetric electrode structures are also well suited for creating large lesions in ventricle regions of the heart. FIG. 36 shows a representative radial asymmetric support structure 146 located for use within the left ventricle. In conformance with the foregoing Criteria Table, the structure 146 occupying the left ventricle is axially symmetric.

The more closely radially spaced longitudinal splines 148 of the structure 146 carry an array of multiple electrodes 150. The electrodes 150 serve as transmitters of ablation energy. The less closely radially spaced longitudinal splines 149 do not carry the electrodes 150.

Preferably, the electrodes 150 are all simultaneously operated in a uni-polar mode, collectively transmitting radio frequency ablation energy for return through an indifferent patch electrode 166 externally attached to the skin of the patient.

The size and spacing of the electrodes 150 shown in FIG. 36 are purposely set in the same relationship manner described in connection with FIG. 31, to create continuous lesion patterns in tissue due to additive heating effects, also as previously described. In the arrangement shown in FIG. 36, the size and spacing relations conducive to additive heating effects are established between adjacent electrodes 150 both longitudinally along each spline 148 as well as radially between each spline 148. As a result (as FIG. 38 shows), the additive heating effects not only span between adjacent electrodes 150 along each spline 148, but also between adjacent electrodes on different adjacent splines 148, thereby creating a continuous large lesion pattern 144 in tissue T, like that shown in FIG. 35.

Preferable (as FIG. 36 shows), the predetermined closely spaced pattern of multiple electrodes 150 for creating large lesions 144 is congregated near the distal hub 24 of the structure 146. Here, the required close radial spacing between splines 148 (and thus between the electrodes 150) can be best maintained. In addition, the splines 148 in this region near the distal hub 24 can be preformed with elastic memory to normally provide a radial bias, which urges the splines 148 toward each other.

VIII. Representative Preferred Constructions

FIGS. 12 to 17 show a preferred embodiment of an electrode support structure 60 (shown fully assembled in FIG. 16) comprising spline elements 62 arranged in a geometry that is both radially and axially asymmetric.

Figure 12:
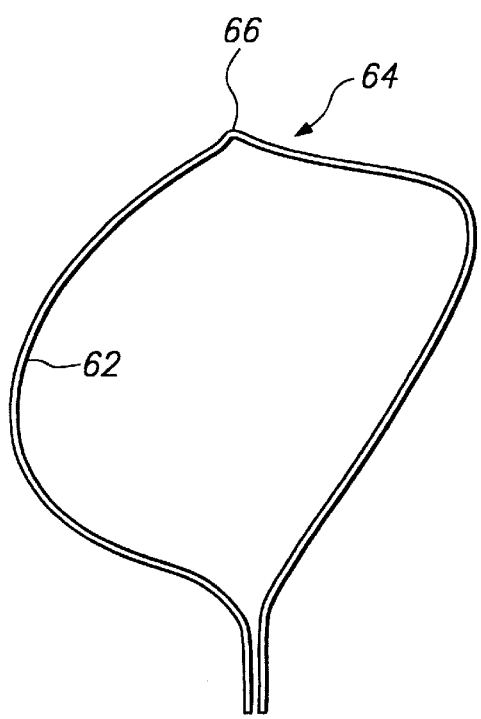
FIG. 12 is a side view of a hoop-like spline body having two spline elements that are axially asymmetric.

As FIG. 12 shows, the structure 60 includes an integral spline body 64 formed by joining together two axially asymmetric spline elements 62. Each body 64 includes a mid-section 66 from which the spline elements 62 extend as an opposed pair of legs. In this arrangement, the body 64 is generally shaped like a lopsided hoop (see FIG. 12). The mid-section 66 includes a preformed detent, whose function will be described later.

The hoop-like body 64 is preferably made from the resilient, inert elastic memory wire, like nickel titanium described above. The body 64 preferably has a rectilinear cross section, to provide increased resistance to twisting about its longitudinal axis. The spline elements 62 are preformed in the desired axially asymmetric shape on opposite sides of the mid-section 66. The axially asymmetric shape generally conforms to the shape earlier shown and described in FIG. 9.

Figure 13:
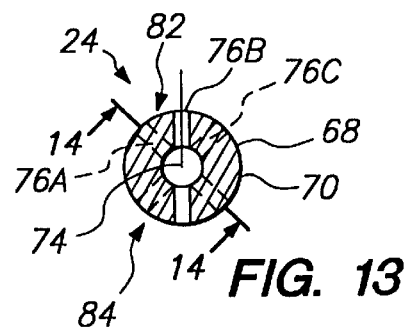
FIG. 13 is a top cross-sectional view of an end cap used in association with the spline body shown in FIG. 12, the end cap providing a radially asymmetric pattern of spline elements.
Figure 14:
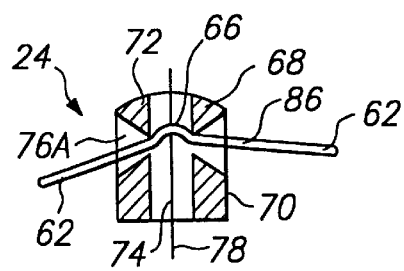
FIG. 14 is a side cross-sectional view of the end cap shown in FIG. 13, with a spline body attached, taken generally along line 14—14 in FIG. 13.
Figure 15:
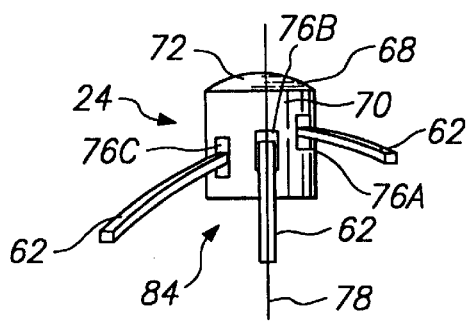
FIG. 15 is an exterior side view of the end cap shown in FIG. 13, with three spline bodies attached in a radially asymmetric pattern.

The distal hub 24 takes the form of an end cap 68 (see FIGS. 13 to 15). The end cap 68 has a generally cylindrical side wall 70 and a rounded end wall 72. A longitudinal bore 74 (see FIGS. 13 and 14) extends through the center of the cap 68.

Slots 76A; 76B; and 76C extend through the cap 68 diametrically across the center bore 74. In the hub 68, the slots 76A–C are generally equally circumferentially spaced within an arcuate segment of about 60°. The axis of each slot 76A–C extends diametrically through the center bore 74. This provides two 90° segments 82 and 84 of slots 76A–C on diametric sides of the cap 68, the slots being circumferentially separated within each segment 82 and 84 by about 45°. The segments 82 and 84 are separated by about 90°. Of course, the slots 76A–C can be formed at other non-uniformly spaced circumferential intervals about the end cap 68. Fewer or more slots can also be provided to achieve the desired asymmetric geometry.

The slots 76A–C are also spaced longitudinally along the bore axis 78. As FIG. 15 best shows, slot 76A is closest to the end wall 72. The slot 76C is farthest from the end wall 72. Intermediate slot 76B is spaced in between the slots 76A and 76C. This spacing allows the spline elements to pass through the hub 68 without interference.

In the illustrated and preferred embodiment, the cap 68 is made of an inert, machined metal, like stainless steel. The bore 74 and slots 76A–C are preferably formed by conventional EDM techniques. Still, other metallic or molded plastic materials can be used to form the cap 68 and associated openings.

A spline leg 62 of the hoop-like body 64 can be inserted through a slot 76A–C until the mid-body section 66 enters the bore 74 (see FIG. 14). The detent in the midsection 66 snaps into the bore 74. This locks the body 64 to the end cap 68, with the opposed pair of asymmetric spline legs 62 radiating free of the respective slot 76A–C. Sequentially inserting three hoop-like bodies 64 in the three slots 76A–D orients and locks the spline elements 62 in the radiating pattern shown in FIG. 16. The three dimension support assembly 60 results (shown in FIG. 16), having a geometry that is both radially and axially asymmetric.

Multiple electrodes 30 can be attached to one or more of the spline elements 62, in the manner shown in pending U.S. application Ser. No. 08/206,414, filed Mar. 4, 1994, which is incorporated herein by reference. In the preferred embodiment, electrodes 30 are provided on the spline elements 62 in the segment 82, but not in the segment 84, in the manner previously described and shown in FIGS. 10 and 11.

In the illustrated and preferred embodiment, the lower surface 86 of the end cap slots 76 is curved (see FIG. 14) The curved lower surface 86 contacts the spline elements 62 (as FIG. 14 shows) when they are bent, or deflected, a prescribed amount. The curvature of the lower slot surface 86 is selected to lend positive support to the spline elements 62 when bent this amount, to prevent spline deflection beyond a minimum bend radius. The bend radius is selected to be above that which failure-mode stresses are most likely to develop in the spline elements 62, which are most likely to occur when the slidable sheath 44 compresses and collapses the spline elements 62 in the manner shown in FIG. 3.

Figures 16, 17:
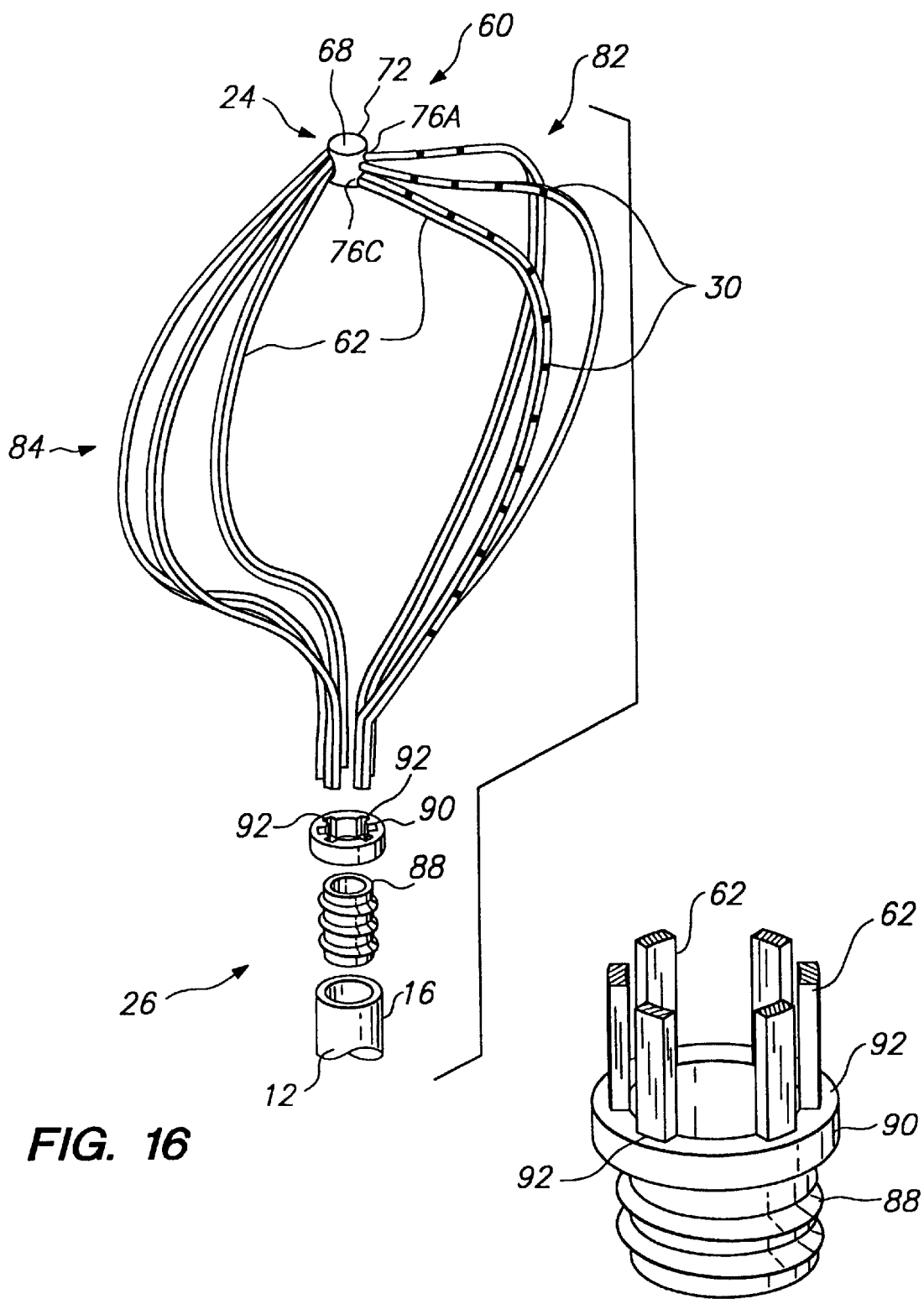
FIG. 16 is an exploded, perspective view of a multiple electrode assembly formed from three axially asymmetric spline bodies in a radially asymmetric geometry.
FIG. 17 is a perspective view of a base that is used in association with the end cap shown in FIGS. 13 to 15 to form the multiple electrode assembly shown in FIG. 16.

In the support structure 60, the base 26 includes an anchor member 88 and a mating lock ring 90 (see FIGS. 16 and 17). The anchor member 88 fits with an interference friction fit into the distal end 16 of the catheter tube 12. The lock ring 90 includes a series of circumferentially spaced grooves 92 into which the free proximal ends of the spline legs 62 fit. The lock ring 90 fits about the anchor member 88 to capture the free ends of the spline legs 62 between the interior surface of the grooves 92 and the outer surface of the anchor member 88 (see FIG. 17).

The anchor member 88/lock ring 90 assembly holds the spline elements 62 in their asymmetric radial spaced relationship while their preformed shape holds them in a desired axially asymmetric flexed condition.

The hoop-like body 64, slotted end cap 68, and anchor member 88/lock ring 90 assembly provide manufacturing efficiencies, as the number of the components parts required to form the asymmetric electrode support assembly 58 is minimized. The slotted cap 68 circumferentially aligns and stabilizes the spline elements 62, both circumferentially and longitudinally. The sequential insert and snap lock process of the attaching the bodies 64 to the slotted cap 68 also significantly simplifies the assembly process.

Figure 18:
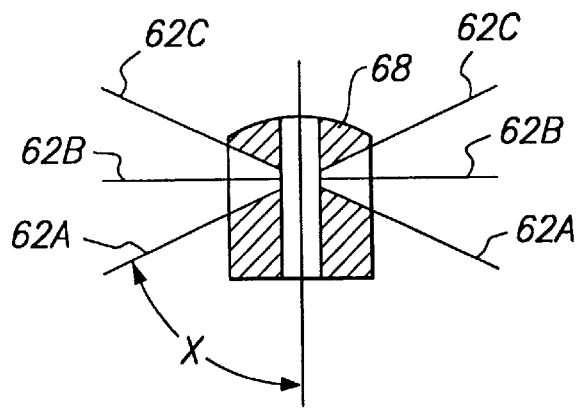
FIG. 18 is a side cross-sectional view of the end cap shown in FIGS. 13 to 15, demonstrating the preferred angular relationship between the spline elements and the end cap.

The preferred structure 60 creates a relatively large distal surface area and small deflection forces, and thus reduces the overall magnitude of pressure exerted against tissue. As FIG. 18 shows, the spline elements 62 of the preferred embodiment extend through the axis of the cap 68 at an angle χ that is greater than about 45° (as shown by spline boundary line 62A in FIG. 18), but is less than about 110° (as shown by spline boundary line 62C in FIG. 18). Preferably, the angle χ is between about 80° and 100°. In the illustrated preferred embodiment (as shown by spline boundary line 62B in FIG. 18), the angle χ is about 90° (i.e., the spline boundary line 62C extends generally perpendicular to the axis of the cap 48).

Figure 19:
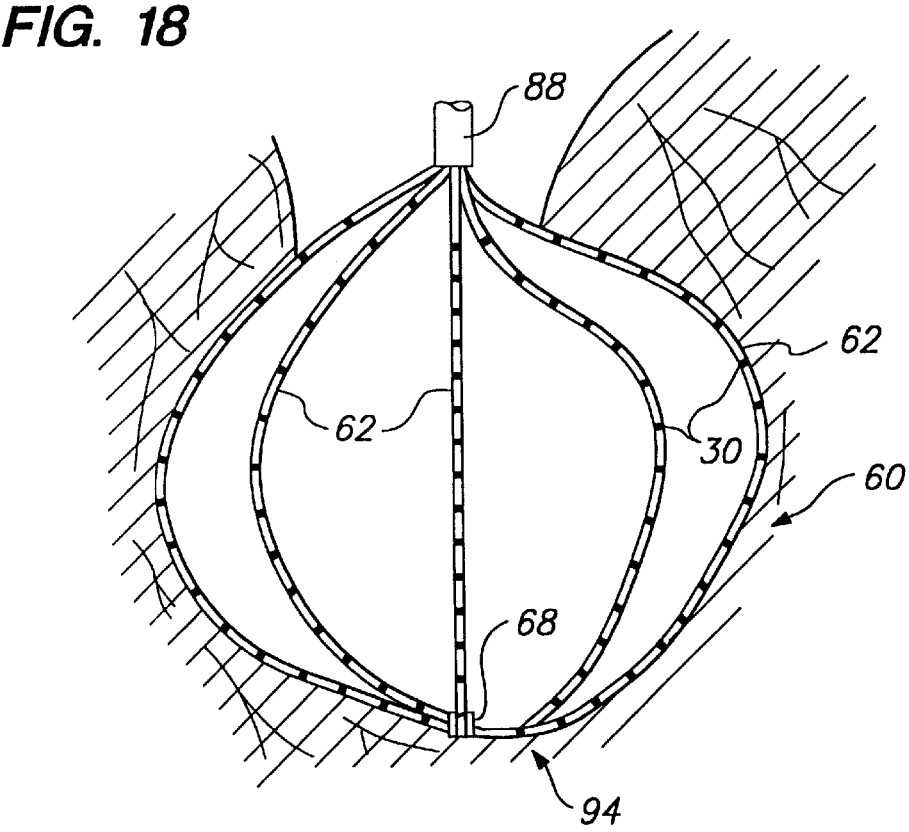
FIG. 19 is a side view of the multiple electrode assembly shown in FIG. 16 in contact with tissue.

As FIG. 19 shows, the angle χ that the cap 68 imposes creates a structure 60 having an enlarged, dome-shaped distal surface area 94. The surface area 94 conforms intimately to endocardial tissue as the heart beats. The slotted structure of the cap 68 makes possible the location of the distal-most spline elements 62 very close to the distal end of the cap 68. As a result (see FIG. 19), when the structure 60 is fully deployed for use, the cap 68 projects only a minimal distance beyond the envelope of the resulting structure 60. Practically speaking, the cap 68 lies essentially within the envelope of the distal surface area 94.

The distal geometry that the cap 68 permits creates a relatively smooth surface area 94 that is essentially free of major projections that can extend to a significant extent into endocardial tissue. The contour of the surface 94 extends along an essentially constant arc from one spline 62, across the end cap 68 to an opposite spline 62. The end cap 68 presents a surface 94 free of outward physiologically significant projections that can poke endocardial tissue to cause blunt tissue trauma. The contoured surface 94 extending about the cap 68 thus minimizes the chances of damage to endocardial tissue during use.

The contoured surface 94 permits access to and intimate contact with tissue in the apex of the heart, at the base of the ventricles. About 6 to 8% of infarcted heart tissue is found to lie within the apex. Therefore, providing non-traumatic access to this region offers considerable diagnostic benefit.

Furthermore, the alignment of the end cap 68 along this contoured surface 94 makes it possible to use the end-cap 68 itself as an electrode. The contour surface 94 and non-projecting end-cap 68 allow the physician to deploy the structure 60 and obtain electrogram signals from the apex of the heart using the end-cap 68 as an electrode. Again, considerable diagnostic benefits result.

Further details of the benefits of the construction shown in FIGS. 16 to 19 are found in copending U.S. application Ser. No. 08/557,790, filed Nov. 13, 1995, and entitled "Multiple Electrode Support Structure Having Optimal Bio-Mechanical Characteristics," which is incorporated herein by reference.

FIGS. 23 to 26 show an alternative embodiment of a distal hub 112 for joining flexible spline wires 114 and 116 together. Instead of using the machine, slotted hub 24 (shown in FIGS. 13 to 15), the distal hub 112 comprises a short length of resilient, small diameter plastic tubing 114, which snugly cinches together the mutually looped ends of two spline wire 116 and 118.

The tubing can be made from any inert plastic material having a resilient memory, which normally urges the tubing bore 115 toward a preset interior diameter. Material made from, for example, polyethylene terepthalate (PET), polyolefin, or composites made from TEFLON™ plastic and KEVLAR™ plastic (for example, a triple laminate of KEVLAR™ plastic sandwiched between two layers of TEFLON™ plastic) can be used. The spline wires 116 and 118 can comprise metal or plastic, as before described. Metal wire made from NITINOL™ material is well suited for this use.

Figure 24:
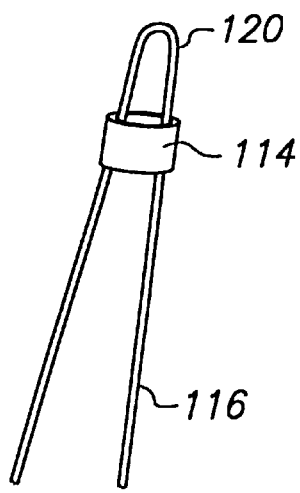
FIGS. 24 to 26 are perspective side views of the assembly of the distal hub assembly shown in FIG. 23.

The tubing 114 is precut to the desired length. As FIG. 24 shows, the first spline wire 116 is bent upon itself and passed as a loop 120 through the bore 115 of the tubing 114. The interior diameter of the tubing bore 115 is selected to snugly engage the bent-over wire 116. The tubing 114 is positioned short of the formed loop 120.

Figure 25:
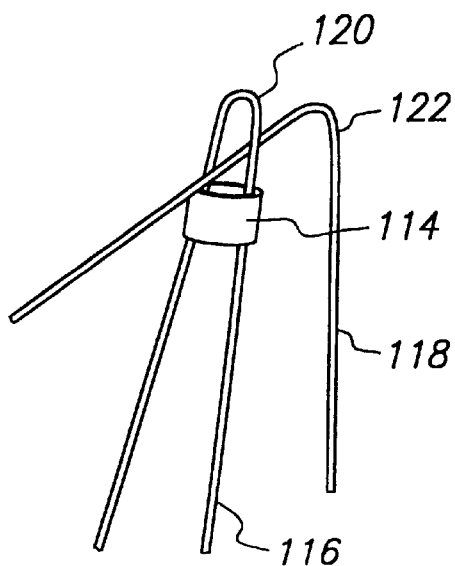

As FIG. 25 shows, the second spline wire 118 is passed, end-first, through the formed loop 120, without passage through the bore 115 of the tubing 114. The spline wire 118 is bent upon itself within the loop 120, forming a second loop 122, which is thereby engaged or "woven" through the first loop 120. Addition lengths of spline wire could also be passed through and bent back over the loop 120 in the same fashion, forming a registration of loops mutually woven through the first loop.

Figure 26:
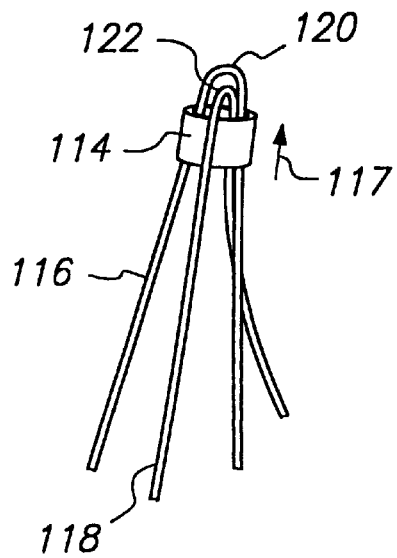

As FIG. 26 shows, the tubing 114 is then slid, like the knot of a necktie, upward along the looped first spline wire 116 (see arrow 117 in FIG. 26). The tubing 144 bears against the woven registration of the loops 120 and 122. The resilient memory of the tubing 114 exerts a force at its distal end to snug holds the woven registration of the loops 120 and 122 together. The free legs of the spline wires 116 and 118, which depend from the tubing 114, can be manually manipulated to achieve the desired radial orientation. These legs, once arranged in the desired orientation, can be connected to the anchor 88 in the manner previously described. Electrodes can be mounted on the free spline legs, also in the way previously described.

FIG. 27 shows another alternative embodiment of a distal hub 124. The hub 124 includes a puncturable material, which is capable of being pierced by threading spline wire 130 end-first through it.

In the illustrated and preferred embodiment, the hub 124 is formed from a precut, short length of rigid tubing 126 made, for example, of a rigid polycarbonate material or a metal material. Through-slots 127 are drilled through the tubing 126, to accommodate passage of spline wires 130. As FIG. 27 also shows, the tubing 126 is encapsulated by a resilient, elastomeric sealing material 128, like silicone rubber or a soft urethane material.

In one embodiment, when the sealing material 128 has cured, individual lengths of spline wire 130 are punched, end-first, into and through the slots 127 of the encapsulated tubing (as shown by arrows 131 in FIG. 28). The spline wire 130 pierces the elastomeric sealing material 128 in passing through the slots 127. Preferably, the elastomeric sealing material 127 is transparent or semi-transparent, to enabling viewing of the slots 127 through it.

Multiple lengths of wire 130 are threaded through the encapsulated material 128 and tubing 126 in the desired orientation to form the desired number of pairs of depending spline legs. Once threaded through, the depending spline legs are secured to the anchor 88 and electrodes attached in the manner previously described.

Alternatively, spline wires 130 can be threaded through the slots 127 of the tubing 126 before encapsulation by the material 128. In this embodiment, the elastomeric material 128 is applied by coating or dipping after the spline wires 130 are threaded through the slots 127.

FIG. 29 shows an alternative embodiment of a support assembly 132. The support assembly 132 includes spline elements 134 radiating in a circumferentially spaced relationship from a center web 136, which constitutes the hub 24.

As FIG. 29 shows, the support assembly 132 is of the type previously shown in FIGS. 21 and 22, which is axially symmetric but radially asymmetric. The support assembly 132 also possesses asymmetric mechanical properties, as already described in connection with FIGS. 21 and 22.

More particularly, the assembly 132 includes seven spline elements 134, designated S1 to S7, arranged in two discrete groups 106 and 108 about a central web 136. The group 106 comprises five adjacent spline elements S1 to S5, and the second group 108 comprises two adjacent spline elements S6 and S7. This provides a radially asymmetric structure, as the difference between the smallest angle β (about 36°) and the largest angle α (about 60°) is greater than 20°.

Furthermore (similar to the structure 104 shown in FIGS. 21 and 22), the splines S6 and S7 (in group 108) are each wider in their transverse direction than each of the splines S1 to S5 (in group 106), and are therefore individually stiffer than the individual splines S1 to S5. This provides the asymmetric of physical properties previously described with reference to the structure 104 in FIGS. 21 and 22.

Figure 30A:
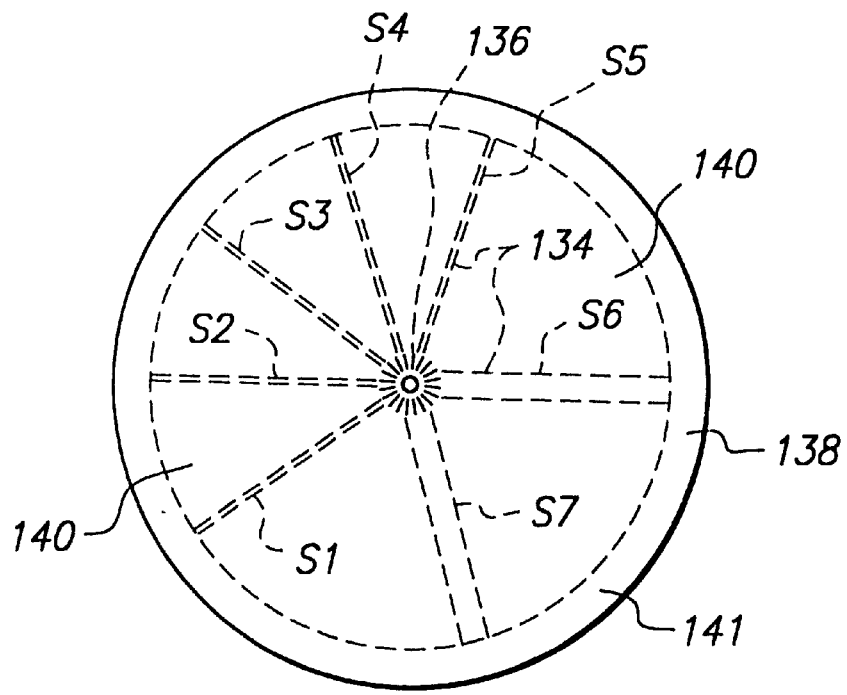
FIGS. 30A and 30B are top views showing the manufacture of the support assembly shown in FIG. 29 by cutting a single sheet of material.

As FIG. 30A shows, the spline elements 134 and web 136 are machined from a single sheet 138 of material. In the illustrated embodiment, the sheet 138 comprises Nickel Titanium stock having a thickness of about 0.004 inch. Other materials, like extruded or molded plastic, or stainless steel can be used for the sheet.

Figure 30B:
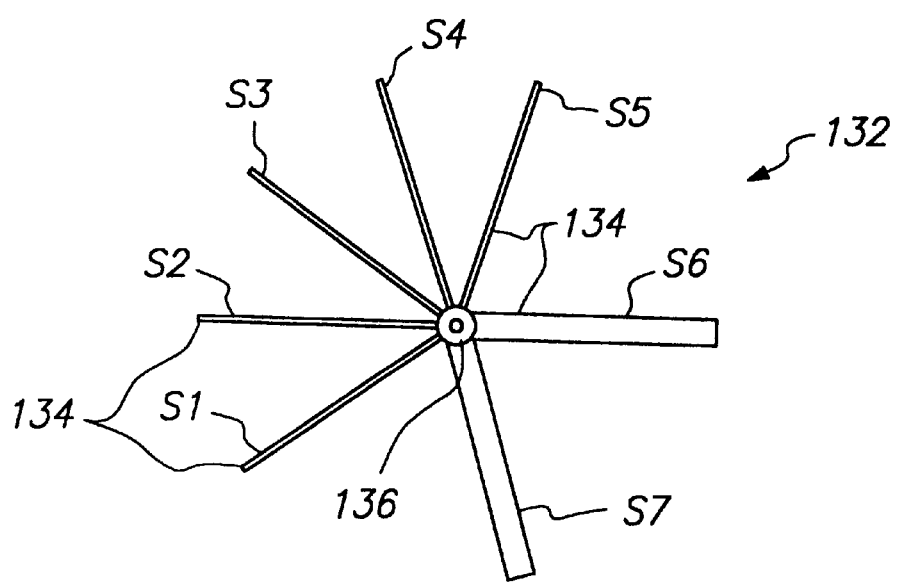

As FIG. 30A also shows, circumferentially spaced, pie shaped segments 140 are initially cut from the sheet 138, leaving behind the spline elements 138 having the desired width and circumferential spacing attached to a peripheral rim 141. The rim 141 is then cut away, leaving the spline elements as shown in FIG. 30B. Laser cutting or another accurate, mechanized cutting technique, like EDM, can be used for this purpose.

One end of the spline elements 138 are connected to the web 136, from which they radiate like spokes. The free ends of the spline elements 138 are connected to the anchor 88 and electrodes attached in the manner previously described.

IX. Deployment of the Support Assemblies

The methodology for deploying each of the symmetric and asymmetric support structures described is generally the same. FIGS. 38A and 38B show a representative deployment technique usable when vascular access to a heart chamber is required.

As FIG. 38A shows, the physician uses an introducer 185, made from inert plastic materials (e.g., polyester), having a skin-piercing cannula 186. The cannula 186 establishes percutaneous access into, for example, the femoral vein 188. The exterior end of the introducer 185 includes a conventional hemostatic valve 190 to block the outflow of blood and other fluids from the access. The valve may take the form of a conventional slotted membrane or conventional shutter valve arrangement (not shown). A valve 190 suitable for use may be commercial procured from, for example, B. Braun Company. The introducer 185 includes a flushing port 187 to introduce sterile saline to periodically clean the region of the valve 190.

As FIG. 38A shows, the physician advances a guide sheath 192 through the introducer 185 into the accessed vein 188. A guide catheter or guide wire (not shown) may be used in association with the guide sheath 192 to aid in directing the guide sheath 192 through the vein 188 toward the heart 194. It should be noted that the views of the heart 194 and other interior regions of the body in this Specification are not intended to be anatomically accurate in every detail. The Figures show anatomic details in diagrammatic form as necessary to show the features of the invention.

The physician observes the advancement of the guide sheath 192 through the vein 188 using fluoroscopic or ultrasound imaging, or the like. The guide sheath 192 can include a radio-opaque compound, such as barium or titanium, for this purpose. Alternatively, a radio-opaque marker can be placed at the distal end of the guide sheath 192.

In this way, the physician maneuvers the guide sheath 192 through the vein 188 into an atrium 196. The guide sheath 192 establishes a passageway through the vein 188 into the atrium 196, without an invasive open heart surgical procedure. Further advancement allows entry into the associated underlying ventricle 198 through the intervening valve 199 (as FIG. 38A shows). If access to the other atrium or ventricle is desired (as FIG. 31 shows), a conventional transeptal sheath assembly (not shown) can be used to gain passage through the septum between the left and right atria.

As FIG. 38A shows, once the guide sheath 192 is placed in the targeted region, the physician advances the catheter tube 12, which carries the structure (generally designated by the letter S in FIGS. 38A and 38B), with the structure S confined within the slidable sheath 44, through the guide sheath 192 and into the targeted region.

As FIG. 38B shows, pulling back upon the slidable sheath 44 (see arrow 200 in FIG. 38B) allows the structure S to spring open within the targeted region for use. The structure S in FIG. 38B is radially asymmetric and axially symmetric.

When deployed for use (as FIG. 38B shows), the three dimensional shape of the support structure S (whether symmetric or asymmetric) holds the spline elements (generally designated by the letter SPL), with associated electrodes (designated by the letter E) in intimate contact against the surrounding tissue mass.

X. Automated Structure Identification

The differences among the support structures disclosed can be characterized in terms of various physical, mechanical, and functional attributes. These attributes include the physical property of the structure, the physical property of the electrodes, and the functional property of the electrode.

The physical property of the structure can include the size of the structure; the shape of the structure; the radial symmetry or asymmetry of the structure; the axial symmetry or asymmetry of the structure; the number of spline elements; or the stiffness value of the spline elements, expressed in terms, for example, of the radial stiffness function $S_r$ discussed above, and whether the stiffness value is symmetric or asymmetric; the recommended criteria for use, as above discussed; or combinations thereof.

The physical property of the electrodes can include the total number of electrodes carried by the structure; the number of electrodes carried per spline element; the distance between electrodes on each spline; the distribution or density pattern of multiple electrodes on the structure; or combinations thereof.

The functional property of the electrodes can include the functionality of the electrodes in terms of a diagnostic capability, such as mapping, or derivation of an electrical characteristic, or pacing, or a therapeutic capability, such as transmission of electrical energy to form a tissue lesion; the characteristics of lesions formed using the structures, whether segmented, large, or long; or combinations thereof.

According to the invention, a family of identification codes is provided for the family 98 of structures. Each identification code uniquely identifies a particular structure in terms of the physical property or properties of the structure or electrode, and in terms of the functional property or properties of the electrodes carried by the structure. An identification element is attached in association with each structure within the family 98 to retain the identification code. The identification element is adapted to provide an output representative of the identification code.

Figure 39:
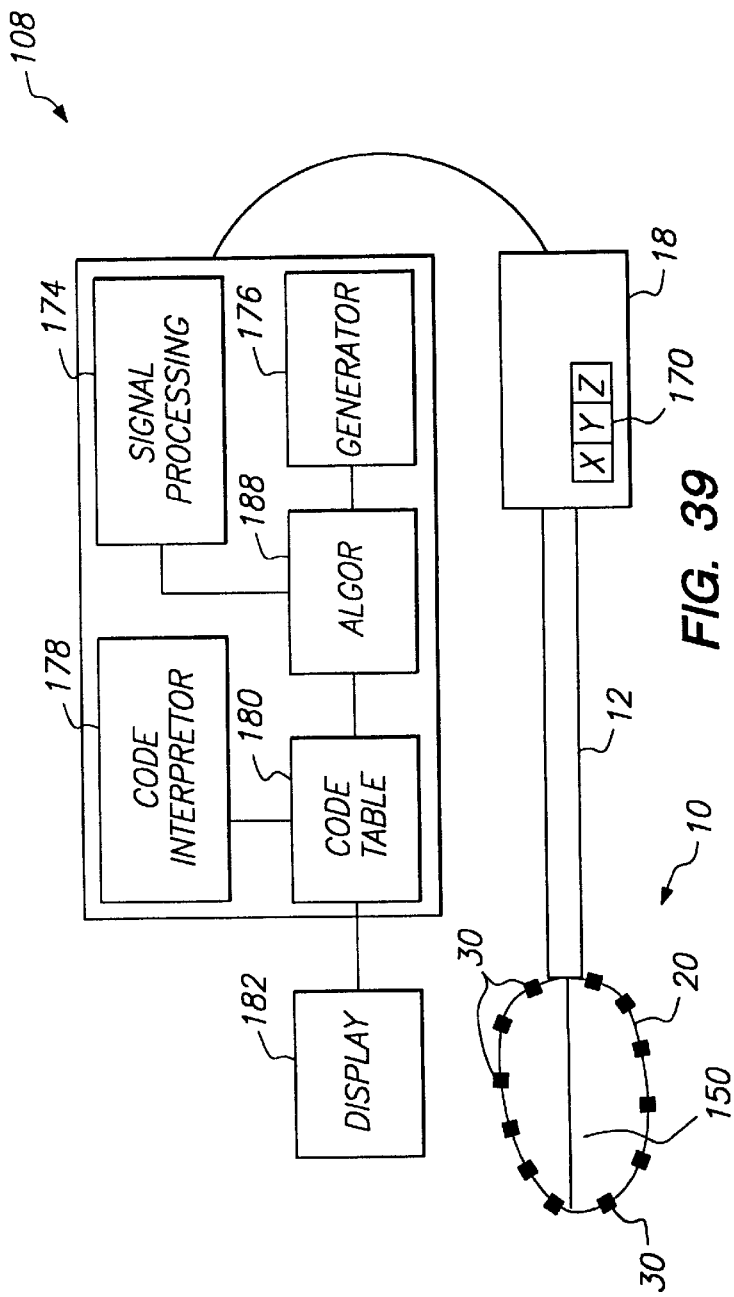
FIG. 39 is a diagrammatic view of a system for identifying the characteristics of a multiple electrode support structure using a machine-readable code, which uniquely identifies the individual physical, mechanical, and functional characteristics of the structure.

In a preferred embodiment (see FIG. 39), each structure 20 carries an identification component 170. The identification component 170 carries the assigned identification code XYZ, which uniquely identifies the individual physical, mechanical, and functional characteristics of the particular structure.

In the illustrated embodiment (see FIG. 39), the coded component 170 is located within the handle 18 of the probe 10 that carries the structure 20. However, the component 170 could be located elsewhere on the probe 10.

The coded component 170 is electrically coupled to an external interpreter 178 when the probe 10 is plugged into a control unit 172 for use. The unit 172 can incorporate a signal processor 174 for processing electrical impulses sensed by the electrodes 30 on the structure 20. The unit 172 can also incorporate, alone or in combination with the signal processor 174, a generator 176 for supplying ablation energy to the electrodes 30.

The interpreter 178 inputs the code XYZ that the coded component 170 contains. The interpreter 178 electronically compares the input code XYZ to, for example, a preestablished master table 180 of codes contained in memory. The master table 180 lists, for each code XYZ, the physical, mechanical, and functional characteristics of the structure 20. The interpreter 178 displays for the physician in understandable alpha/numeric format the physical, mechanical, and functional characteristics of the structure 20 that the code XYZ signifies in the table 180.

The control unit 172 can also include functional algorithms 188 coupled to the processor 174 or generator 176, which set operating parameters based upon the code XYZ. For example, the code XYZ could cause an algorithm to set and control power limits for the generator 176. As another example, the code XYZ can provide input to tissue mapping algorithms, or electrical characteristic derivation algorithms, or provide interpolation for evaluating electrograms between electrodes, or extrapolate sensed electrical activities to locate potential ablation sites, or create a positioning matrix using the electrodes, to help guide ancillary probes within the structure. Further details of establishing a localized coordinate matrix within a multiple electrode structure for the purpose of locating and guiding a movable electrode within the structure are found in copending patent application Ser. No. 08/320,301, filed Oct. 11, 1994 and entitled "Systems and Methods for Guiding Movable Electrode Elements Within Multiple Electrode Structures." This application is incorporated herein by reference.

Figure 40:
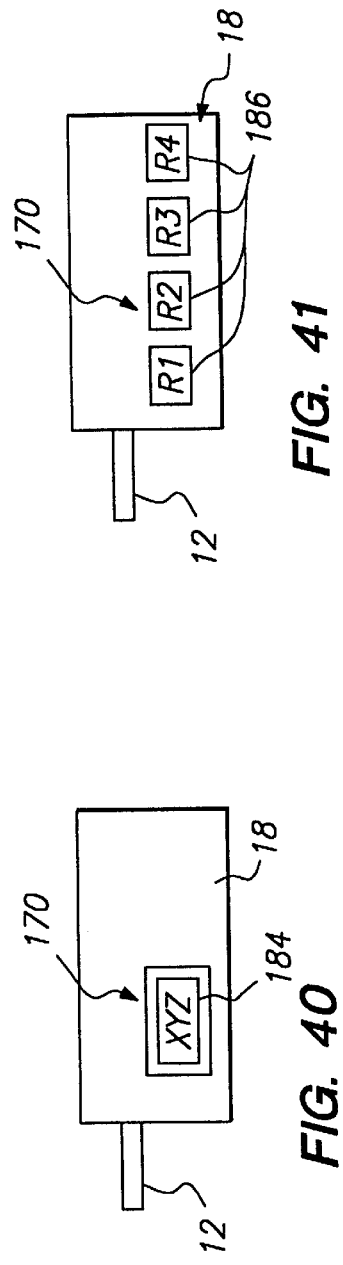
FIG. 40 is a diagrammatic view of one implementation of the machine-readable code used to identify the individual physical, mechanical, and functional characteristics of the support structure shown in FIG. 39.

The coded component 170 can be variously constructed. It can, for example, take the form of an integrated circuit 184 (see FIG. 40), which expresses in digital form the code XYZ for input in RON chips, EPROM chips, RAM chips, resistors, capacitors, programmed logic devices (PLD's), or diodes. Examples of catheter identification techniques of this type are shown in Jackson et al. U.S. Pat. No. 5,383,874, which is incorporated herein by reference.

Figure 41:
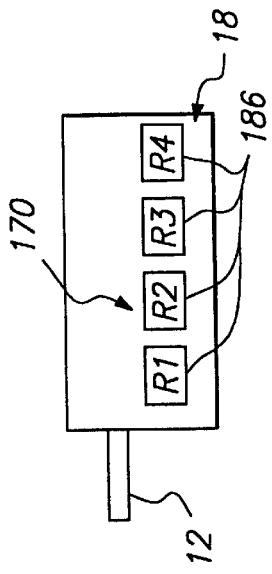
FIG. 41 is a diagrammatic view of another implementation of the machine-readable code used to identify the individual physical, mechanical, and functional characteristics of the support structure shown in FIG. 39.

Alternatively, the coded component 170 can comprise separate electrical elements 186 (see FIG. 41), each one of which expressing an individual characteristic. For example, the electrical elements 186 can comprise resistors (R1 to R4), comprising different resistance values, coupled in parallel. The interpreter 178 measures the resistance value of each resistor R1 to R4. The resistance value of the first resistor R1 expresses in preestablished code, for example, the number of electrodes on the structure. The resistance value of the second resistor R2 expresses in preestablished code, for example, the distribution of electrodes on the structure. The resistance value of the third resistor R3 expresses in preestablished code, for example, the radial symmetry or asymmetry of the structure. The resistance value of the fourth resistor R4 expresses in preestablished code, for example, the axial symmetry or asymmetry of the structure.

In the preferred embodiment, the code XYZ includes code segments, X and Y and Z. Each code segment represents a physical or functional property, or a group of related physical or functional properties.

The segmentation of the code XYZ can, of course, vary. As one example, the X segment can carry identification values representing the shape and size of the structure; the Y segment can carry identification values representing distribution of spline elements and electrodes on the structure; and the Z segment can carry identification values representing the number of splines and the number of electrodes per spline.

The following Table demonstrates a representative segmented code scheme.

| Physical/Functional Property | Code Value | Code Segment (Place) |
| --- | --- | --- |
| Shape | | |
| Axially Symmetric | 01 | X(1) |
| Axially Asymmetric | 02 | X(1) |
| Size | | |
| Diameter 1 | 11 | X(2) |
| Diameter 2 | 12 | X(2) |
| Diameter 3 | 13 | X(2) |
| Diameter 4 | 14 | X(2) |
| Spline Distribution | | |
| Radially Symmetric | 01 | Y(1) |
| Radially Asymmetric | 02 | Y(1) |
| Electrode Distribution | | |
| All Splines | 11 | Y(2) |
| First Spline Group Only | 12 | Y(2) |
| Second Spline Group Only | 13 | Y(2) |
| Number of Spline Elements | | |
| 4 | 01 | Z(1) |
| 6 | 02 | Z(2) |
| 10 | 03 | Z(3) |
| Number of Electrodes Per Spline Element | | |
| 6 | 11 | Z(2) |
| 8 | 12 | Z(2) |
| 10 | 13 | Z(2) |

A representative segmented identification code based upon the above Table could be:

0112 0111 0213 where:

the X(1) segment 01 identifies the structure shape as being axially symmetric;

the X(2) segment 12 identifies the structure size as being Diameter 2;

the Y(1) segment 01 identifies the distribution of spline elements as being radially symmetric;

the Y(2) segment 11 identifies the electrode distribution as being on all spline elements;

the Z(1) segment 02 identifies the presence of six spline elements; and the Z(2) segment 13 identifies the presence of ten electrodes on each spline element.

Multiple resistors R1 to R3 can be used to express this segmented code, with resistor R1 having a resistance value of 112 (expressing the X segment); resistor R2 having a resistance value of 111 (expressing the Y segment); and resistor R3 having a resistance value of 213 (expressing the Z segment). The interpreter 178 measures the resistance value of each resistor R1 to R3 and compares these values to the preestablished master table 180 of codes contained in memory to derive the physical and functional characteristics of the particular structure 20.

The features of the invention are set forth in the following claims.

We claim:

1. An assembly to support a therapeutic or diagnostic element in contact with endothelial tissue in an interior body region, comprising:

a plurality of spline elements assembled in a spaced apart relationship disposed about an axis and generally extending longitudinally along the axis, the spline elements forming a basket structure, each spline element configured for being placed in a convex geometry for contacting the endothelial tissue, a first spline element having a supporting structure exhibiting a first cross-sectional mechanical property, and a second spline element having a supporting structure exhibiting a second cross-sectional mechanical property, the second cross-sectional mechanical property being different than the first cross-sectional mechanical property.

2. An assembly according to claim 1 wherein the first spline element is generally diametrically spaced across the axis from the second spline element.

3. An assembly according to claim 2 and further including at least one of a therapeutic element and a diagnostic element carried by the first spline element.

4. An assembly according to claim 3 wherein the second spline element is free of a therapeutic element and a diagnostic element.

5. An assembly according to claim 1 and further including at least one of a therapeutic element and a diagnostic element carried by the first spline element.

6. An assembly according to claim 5 wherein the second spline element is free of a therapeutic element and a diagnostic element.

7. An assembly according to claim 2, 4, or 6 wherein the at least one therapeutic element and diagnostic element comprises an electrode.

8. An assembly according to claim 7 wherein the electrode is adapted to transmit electrical energy.

9. An assembly according to claim 7 wherein the electrode is adapted to transmit ablation energy.

10. An assembly according to claim 7 wherein the electrode is adapted to transmit or sense electrical signals.

11. An assembly according to claim 1 wherein the first spline element occupies a first area of the structure, and wherein the second spline element occupies a second area of the structure less than the first area.

12. An assembly according to claim 11 and further including at least one of a therapeutic element and a diagnostic element carried by the first spline element.

13. An assembly according to claim 11 wherein the second spline element is free of a therapeutic element and a diagnostic element.

14. An assembly according to claim 1 wherein the first and second spline elements are preformed with a convex bias.

15. An assembly according to claim 14 further including at least one of a therapeutic element and a diagnostic element carried by the first spline element.

16. An assembly according to claim 15 wherein the second spline element is free of a therapeutic element and a diagnostic element.

17. An assembly according to claim 1 wherein the first spline element is affixed to the second spline element at a proximal region and a distal region.

18. An assembly according to claim 17 further including at least one of a therapeutic element and a diagnostic element carried by the first spline element.

19. An assembly according to claim 18 wherein the second spline element is free of a therapeutic element and a diagnostic element.

20. An assembly according to claim 1 wherein the first spline element has a first width and the second spline element has a second width greater than the first width.

21. An assembly according to claim 20 further including at least one of a therapeutic element and a diagnostic element carried by the first spline element.

22. An assembly according to claim 21 wherein the second spline element is free of a therapeutic element and a diagnostic element.

23. An assembly for deployment in an interior body region, comprising:

a plurality of spline elements assembled in a spaced apart relationship about an axis and configured for being placed in a convex geometry for contacting endothelial tissue, the spline elements being disposed about the axis and generally extending longitudinally along the axis, the spline elements forming a basket structure, the spline elements including a first group having support structure exhibiting first cross-sectional mechanical properties, and a second group having support structure exhibiting second cross-sectional mechanical properties different than the respective first cross-sectional mechanical properties, the first group comprising a greater number of spline elements than the second group.

24. An assembly according to claim 23 wherein the first group is generally diametrically spaced across the axis from the second group.

25. An assembly according to claim 23 wherein the spline elements in the first group are mutually spaced closer together than the spline elements in the second group.

26. An assembly according to claim 23 wherein the first group occupies a first area, and wherein the second group occupies a second area less than the first area.

27. An assembly according to claim 23 and further including at least one of a therapeutic element and a diagnostic element carried by the first group.

28. An assembly according to claim 27 wherein the second group is free of a therapeutic element and a diagnostic element carried by the first spline element.

29. An assembly according to claim 27 wherein the at least one therapeutic element and diagnostic element comprises an electrode.

30. An assembly according to claim 29 wherein the electrode is adapted to transmit electrical energy.

31. An assembly according to claim 29 wherein the electrode is adapted to transmit ablation energy.

32. An assembly according to claim 29 wherein the electrode is adapted to transmit or sense electrical signals.

33. An assembly according to claim 23 wherein the respective first and second groups of spline elements are preformed with a convex bias.

34. An assembly according to claim 33 further including at least one of a therapeutic element and a diagnostic element carried by each of the first group of spline elements.

35. An assembly according to claim 34 wherein each of the second group of spline elements is free of a therapeutic element and a diagnostic element.

36. An assembly according to claim 23 wherein the first group of spline elements are affixed to the second group of spline elements at a proximal region and a distal region.

37. An assembly according to claim 36 further including at least one of a therapeutic element and a diagnostic element carried by each of the first group of spline elements.

38. An assembly according to claim 37 wherein each of the second group of spline elements are free of a therapeutic element and a diagnostic element.

39. An assembly according to claim 23 wherein the first group of spline elements have a first width and the second group of spline elements have a second width greater than the first width.

40. An assembly according to claim 39 further including at least one of a therapeutic element and a diagnostic element carried by each of the first group of spline elements.

41. An assembly according to claim 40 wherein each of the second group of spline elements is free of a therapeutic element and a diagnostic element.

* * * * *